(12) United States Patent
DiCarlo et al.

(10) Patent No.: US 8,216,612 B2
(45) Date of Patent: *Jul. 10, 2012

(54) EMBOLIZATION

(75) Inventors: Paul DiCarlo, Middleboro, MA (US); Thomas V. Casey, II, Grafton, MA (US); Stephan P. Mangin, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 81 days.

This patent is subject to a terminal disclaimer.

(21) Appl. No.: 12/769,172

(22) Filed: Apr. 28, 2010

(65) Prior Publication Data

US 2010/0209522 A1      Aug. 19, 2010

Related U.S. Application Data

(63) Continuation of application No. 10/791,552, filed on Mar. 2, 2004, now Pat. No. 7,736,671.

(51) Int. Cl.
*A61K 9/14* (2006.01)

(52) U.S. Cl. ...................................................... 424/489

(58) Field of Classification Search ........................ None
See application file for complete search history.

(56) References Cited

U.S. PATENT DOCUMENTS

| | | | |
|---|---|---|---|
| 2,275,154 A | 3/1942 | Merrill et al. |
| 2,609,347 A | 9/1952 | Wilson |
| 3,615,972 A | 10/1971 | Morehouse et al. |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,402,319 A | 9/1983 | Handa et al. |
| 4,413,070 A | 11/1983 | Rembaum |
| 4,427,794 A | 1/1984 | Lange et al. |
| 4,428,869 A | 1/1984 | Munteanu et al. |
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Mosier |
| 4,515,906 A | 5/1985 | Friesen et al. |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,573,967 A | 3/1986 | Hargrove et al. |
| 4,622,362 A | 11/1986 | Rembaum |
| 4,623,706 A | 11/1986 | Timm et al. |
| 4,629,464 A | 12/1986 | Takata et al. |
| 4,640,807 A | 2/1987 | Afghan et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,674,480 A | 6/1987 | Lemelson |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,695,466 A | 9/1987 | Morishita et al. |
| 4,713,076 A | 12/1987 | Draenert |
| 4,742,086 A | 5/1988 | Masamizu et al. |
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,793,980 A | 12/1988 | Torobin |
| 4,795,741 A | 1/1989 | Leshchiner et al. |
| 4,801,458 A | 1/1989 | Hidaka et al. |
| 4,804,366 A | 2/1989 | Zdeb et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |
| 4,859,711 A | 8/1989 | Jain et al. |
| 4,863,972 A | 9/1989 | Itagaki et al. |
| 4,897,255 A | 1/1990 | Fritzberg et al. |
| 4,929,400 A | 5/1990 | Rembaum et al. |
| 4,933,372 A | 6/1990 | Feibush et al. |
| 4,946,899 A | 8/1990 | Kennedy et al. |

(Continued)

FOREIGN PATENT DOCUMENTS

AU        A-76186/98        10/1998

(Continued)

OTHER PUBLICATIONS

Abbara et al., "Transcervical Expulsion of a Fibroid as a Result of Uterine Artery Embolization for Leiomyomata", *JVIR*, vol. 10, No. 4, pp. 409-411, 1999.

(Continued)

*Primary Examiner* — Alton Pryor

(74) *Attorney, Agent, or Firm* — Bingham McCutchen LLP

(57) ABSTRACT

Embolization, as well as related particles, compositions, and methods, are disclosed.

33 Claims, 5 Drawing Sheets

U.S. PATENT DOCUMENTS

| | | |
|---|---|---|
| 4,954,399 A | 9/1990 | Tani et al. |
| 4,981,625 A | 1/1991 | Rhim et al. |
| 4,990,340 A | 2/1991 | Hidaka et al. |
| 4,999,188 A | 3/1991 | Sloldovnik et al. |
| 5,007,940 A | 4/1991 | Berg |
| 5,011,677 A | 4/1991 | Day et al. |
| H915 H | 5/1991 | Gibbs |
| 5,015,423 A | 5/1991 | Eguchi et al. |
| 5,032,117 A | 7/1991 | Motta |
| 5,034,324 A | 7/1991 | Shinozaki et al. |
| 5,047,438 A | 9/1991 | Feibush et al. |
| 5,079,274 A | 1/1992 | Schneider et al. |
| 5,091,205 A | 2/1992 | Fan |
| 5,106,903 A | 4/1992 | Vanderhoff et al. |
| 5,114,421 A | 5/1992 | Polak |
| 5,116,387 A | 5/1992 | Berg |
| 5,120,349 A | 6/1992 | Stewart et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,158,573 A | 10/1992 | Berg |
| 5,171,214 A | 12/1992 | Kolber et al. |
| 5,171,217 A | 12/1992 | March et al. |
| 5,181,921 A | 1/1993 | Makita et al. |
| 5,190,760 A | 3/1993 | Baker |
| 5,190,766 A | 3/1993 | Ishihara |
| 5,192,301 A | 3/1993 | Kamiya et al. |
| 5,202,352 A | 4/1993 | Okada et al. |
| 5,216,096 A | 6/1993 | Hattori et al. |
| 5,253,991 A | 10/1993 | Yokota et al. |
| 5,260,002 A | 11/1993 | Wang |
| 5,262,176 A | 11/1993 | Palmacci et al. |
| 5,263,992 A | 11/1993 | Guire |
| 5,288,763 A | 2/1994 | Li et al. |
| 5,292,814 A | 3/1994 | Bayer et al. |
| 5,302,369 A | 4/1994 | Day et al. |
| 5,314,974 A | 5/1994 | Ito et al. |
| 5,316,774 A | 5/1994 | Eury et al. |
| RE34,640 E | 6/1994 | Kennedy et al. |
| 5,320,639 A | 6/1994 | Rudnick |
| 5,328,936 A | 7/1994 | Leifholtz et al. |
| 5,336,263 A | 8/1994 | Ersek et al. |
| 5,344,452 A | 9/1994 | Lemperle |
| 5,344,867 A | 9/1994 | Morgan et al. |
| 5,354,290 A | 10/1994 | Gross |
| 5,369,133 A | 11/1994 | Ihm et al. |
| 5,369,163 A | 11/1994 | Chiou et al. |
| 5,382,260 A | 1/1995 | Dormandy, Jr. et al. |
| 5,384,124 A | 1/1995 | Courteille et al. |
| 5,397,303 A | 3/1995 | Sancoff et al. |
| 5,398,851 A | 3/1995 | Sancoff et al. |
| 5,403,870 A | 4/1995 | Gross |
| 5,417,982 A | 5/1995 | Modi |
| 5,431,174 A | 7/1995 | Knute |
| 5,435,645 A | 7/1995 | Faccioli et al. |
| 5,443,495 A | 8/1995 | Buscemi et al. |
| 5,456,693 A | 10/1995 | Conston et al. |
| 5,468,801 A | 11/1995 | Antonelli et al. |
| 5,469,854 A | 11/1995 | Unger et al. |
| 5,476,472 A | 12/1995 | Dormandy, Jr. et al. |
| 5,484,584 A | 1/1996 | Wallace et al. |
| 5,490,984 A | 2/1996 | Freed |
| 5,494,682 A | 2/1996 | Cohen et al. |
| 5,494,940 A | 2/1996 | Unger et al. |
| 5,512,604 A | 4/1996 | Demopolis |
| 5,514,090 A | 5/1996 | Kriesel et al. |
| 5,525,334 A | 6/1996 | Ito et al. |
| 5,534,589 A | 7/1996 | Hager et al. |
| 5,541,031 A | 7/1996 | Yamashita et al. |
| 5,542,935 A | 8/1996 | Unger et al. |
| 5,553,741 A | 9/1996 | Sancoff et al. |
| 5,556,391 A | 9/1996 | Cercone et al. |
| 5,556,610 A | 9/1996 | Yan et al. |
| 5,558,255 A | 9/1996 | Sancoff et al. |
| 5,558,822 A | 9/1996 | Gitman et al. |
| 5,558,856 A | 9/1996 | Klaveness et al. |
| 5,559,266 A | 9/1996 | Klaveness et al. |
| 5,567,415 A | 10/1996 | Porter |
| 5,569,193 A | 10/1996 | Hofstetter et al. |
| 5,569,449 A | 10/1996 | Klaveness et al. |
| 5,569,468 A | 10/1996 | Modi |
| 5,571,182 A | 11/1996 | Ersek et al. |
| 5,580,575 A | 12/1996 | Unger et al. |
| 5,583,162 A | 12/1996 | Li et al. |
| 5,585,112 A | 12/1996 | Unger et al. |
| 5,595,821 A | 1/1997 | Hager et al. |
| 5,622,657 A | 4/1997 | Takada et al. |
| 5,624,685 A | 4/1997 | Takahashi et al. |
| 5,635,215 A | 6/1997 | Boschetti et al. |
| 5,637,087 A | 6/1997 | O'Neil et al. |
| 5,639,710 A | 6/1997 | Lo et al. |
| 5,648,095 A | 7/1997 | Illum et al. |
| 5,648,100 A | 7/1997 | Boschetti et al. |
| 5,650,116 A | 7/1997 | Thompson |
| 5,651,990 A | 7/1997 | Takada et al. |
| 5,653,922 A | 8/1997 | Li et al. |
| 5,657,756 A | 8/1997 | Vrba |
| 5,681,576 A | 10/1997 | Henry |
| 5,695,480 A | 12/1997 | Evans et al. |
| 5,695,740 A | 12/1997 | Porter |
| 5,698,271 A | 12/1997 | Liberti et al. |
| 5,701,899 A | 12/1997 | Porter |
| 5,715,824 A | 2/1998 | Unger et al. |
| 5,716,981 A | 2/1998 | Hunter et al. |
| 5,718,884 A | 2/1998 | Klaveness et al. |
| 5,723,269 A | 3/1998 | Akagi et al. |
| 5,725,534 A | 3/1998 | Rasmussen |
| 5,733,925 A | 3/1998 | Kunz et al. |
| 5,741,331 A | 4/1998 | Pinchuk |
| 5,746,734 A | 5/1998 | Dormandy, Jr. et al. |
| 5,752,974 A | 5/1998 | Rhee et al. |
| 5,756,127 A | 5/1998 | Grisoni et al. |
| 5,760,097 A | 6/1998 | Li et al. |
| 5,766,147 A | 6/1998 | Sancoff et al. |
| 5,770,222 A | 6/1998 | Unger et al. |
| 5,779,668 A | 7/1998 | Grabenkort |
| 5,785,642 A | 7/1998 | Wallace et al. |
| 5,785,682 A | 7/1998 | Grabenkort |
| 5,792,478 A | 8/1998 | Lawin et al. |
| 5,795,562 A | 8/1998 | Klaveness et al. |
| 5,797,953 A | 8/1998 | Tekulve |
| 5,807,323 A | 9/1998 | Kriesel et al. |
| 5,813,411 A | 9/1998 | Van Bladel et al. |
| 5,823,198 A | 10/1998 | Jones et al. |
| 5,827,502 A | 10/1998 | Klaveness et al. |
| 5,827,531 A | 10/1998 | Morrison et al. |
| 5,830,178 A | 11/1998 | Jones et al. |
| 5,833,361 A | 11/1998 | Funk |
| 5,840,387 A | 11/1998 | Berlowitz-Tarrant et al. |
| 5,846,518 A | 12/1998 | Yan et al. |
| 5,853,752 A | 12/1998 | Unger et al. |
| 5,855,615 A | 1/1999 | Bley et al. |
| 5,863,957 A | 1/1999 | Li et al. |
| 5,876,372 A | 3/1999 | Grabenkort et al. |
| 5,877,224 A | 3/1999 | Brocchini et al. |
| 5,885,216 A | 3/1999 | Evans, III et al. |
| 5,885,547 A | 3/1999 | Gray |
| 5,888,546 A | 3/1999 | Ji et al. |
| 5,888,930 A | 3/1999 | Smith et al. |
| 5,891,155 A | 4/1999 | Irie |
| 5,894,022 A | 4/1999 | Ji et al. |
| 5,895,398 A | 4/1999 | Wensel et al. |
| 5,895,411 A | 4/1999 | Irie |
| 5,899,877 A | 5/1999 | Leibitzki et al. |
| 5,902,832 A | 5/1999 | Van Bladel et al. |
| 5,902,834 A | 5/1999 | Porrvik |
| 5,922,025 A | 7/1999 | Hubbard |
| 5,922,304 A | 7/1999 | Unger |
| 5,928,626 A | 7/1999 | Klaveness et al. |
| 5,935,553 A | 8/1999 | Unger et al. |
| 5,951,160 A | 9/1999 | Ronk |
| 5,957,848 A | 9/1999 | Sutton et al. |
| 5,959,073 A | 9/1999 | Schlameus et al. |
| 6,003,566 A | 12/1999 | Thibault et al. |
| 6,015,546 A | 1/2000 | Sutton et al. |
| 6,027,472 A | 2/2000 | Kriesel et al. |

| | | | |
|---|---|---|---|
| 6,028,066 A | 2/2000 | Unger | |
| 6,047,861 A | 4/2000 | Vidal et al. | |
| 6,048,908 A | 4/2000 | Kitagawa | |
| 6,051,247 A | 4/2000 | Hench et al. | |
| 6,056,721 A | 5/2000 | Shulze | |
| 6,056,844 A | 5/2000 | Guiles et al. | |
| 6,059,766 A | 5/2000 | Greff | |
| 6,063,068 A | 5/2000 | Fowles et al. | |
| 6,071,495 A | 6/2000 | Unger et al. | |
| 6,071,497 A | 6/2000 | Steiner et al. | |
| 6,073,759 A | 6/2000 | Lamborne et al. | |
| 6,077,256 A | 6/2000 | Mann | |
| 6,090,925 A | 7/2000 | Woiszwillo et al. | |
| 6,096,344 A | 8/2000 | Liu et al. | |
| 6,099,064 A | 8/2000 | Lund | |
| 6,099,864 A | 8/2000 | Morrison et al. | |
| 6,100,306 A | 8/2000 | Li et al. | |
| 6,139,963 A | 10/2000 | Fujii et al. | |
| 6,149,623 A | 11/2000 | Reynolds | |
| 6,149,664 A | 11/2000 | Kurz | |
| 6,160,084 A | 12/2000 | Langer et al. | |
| 6,162,377 A | 12/2000 | Ghosh et al. | |
| 6,165,193 A | 12/2000 | Greene, Jr. et al. | |
| 6,179,817 B1 | 1/2001 | Zhong | |
| 6,191,193 B1 | 2/2001 | Lee et al. | |
| 6,214,331 B1 | 4/2001 | Vanderhoff et al. | |
| 6,214,384 B1 | 4/2001 | Pallado et al. | |
| 6,224,630 B1 | 5/2001 | Bao et al. | |
| 6,224,794 B1 | 5/2001 | Amsden et al. | |
| 6,235,224 B1 | 5/2001 | Mathiowitz et al. | |
| 6,238,403 B1 | 5/2001 | Greene, Jr. et al. | |
| 6,245,090 B1 | 6/2001 | Gilson et al. | |
| 6,251,661 B1 | 6/2001 | Urabe et al. | |
| 6,258,338 B1 | 7/2001 | Gray | |
| 6,261,585 B1 | 7/2001 | Sefton et al. | |
| 6,264,861 B1 | 7/2001 | Tavernier et al. | |
| 6,267,154 B1 | 7/2001 | Felicelli et al. | |
| 6,268,053 B1 | 7/2001 | Woiszwillo et al. | |
| 6,277,392 B1 | 8/2001 | Klein | |
| 6,280,457 B1 | 8/2001 | Wallace et al. | |
| 6,291,605 B1 | 9/2001 | Freeman et al. | |
| 6,296,604 B1 | 10/2001 | Garibaldi et al. | |
| 6,296,622 B1 | 10/2001 | Kurz et al. | |
| 6,296,632 B1 | 10/2001 | Luscher et al. | |
| 6,306,418 B1 | 10/2001 | Bley | |
| 6,306,419 B1 | 10/2001 | Vachon et al. | |
| 6,306,425 B1 | 10/2001 | Tice et al. | |
| 6,306,427 B1 | 10/2001 | Annonier et al. | |
| 6,312,407 B1 | 11/2001 | Zadno-Azizi et al. | |
| 6,312,942 B1 | 11/2001 | Plüss-Wenzinger et al. | |
| 6,315,709 B1 | 11/2001 | Garibaldi et al. | |
| 6,335,384 B1 | 1/2002 | Evans et al. | |
| 6,344,182 B1 | 2/2002 | Sutton et al. | |
| 6,355,275 B1 | 3/2002 | Klein | |
| 6,358,238 B1 | 3/2002 | Sherry | |
| 6,368,658 B1 | 4/2002 | Schwarz et al. | |
| 6,379,373 B1 | 4/2002 | Sawhney et al. | |
| 6,388,043 B1 | 5/2002 | Langer et al. | |
| 6,394,965 B1 | 5/2002 | Klein | |
| 6,423,332 B1 | 7/2002 | Huxel et al. | |
| 6,432,437 B1 | 8/2002 | Hubbard | |
| 6,436,112 B2 | 8/2002 | Wensel et al. | |
| 6,443,941 B1 | 9/2002 | Slepian et al. | |
| 6,458,296 B1 | 10/2002 | Heinzen et al. | |
| 6,476,069 B2 | 11/2002 | Krall et al. | |
| 6,495,155 B1 | 12/2002 | Tice et al. | |
| 6,544,503 B1 | 4/2003 | Vanderhoff et al. | |
| 6,544,544 B2 | 4/2003 | Hunter et al. | |
| 6,545,097 B2 | 4/2003 | Pinchuk et al. | |
| 6,575,896 B2 | 6/2003 | Silverman et al. | |
| 6,602,261 B2 | 8/2003 | Greene, Jr. et al. | |
| 6,602,524 B2 | 8/2003 | Batich et al. | |
| 6,605,111 B2 | 8/2003 | Bose et al. | |
| 6,629,947 B1 | 10/2003 | Sahatjian et al. | |
| 6,632,531 B2 | 10/2003 | Blankenship | |
| 6,652,883 B2 | 11/2003 | Goupil et al. | |
| 6,680,046 B1 | 1/2004 | Boschetti | |
| 6,699,222 B1 | 3/2004 | Jones et al. | |
| 6,998,137 B2 | 2/2006 | Shih et al. | |
| 7,311,861 B2 | 12/2007 | Lanphere et al. | |
| 7,449,236 B2 | 11/2008 | Lanphere et al. | |
| 7,462,366 B2 | 12/2008 | Lanphere et al. | |
| 7,736,671 B2 * | 6/2010 | DiCarlo et al. | 424/489 |
| 2001/0001835 A1 | 5/2001 | Greene, Jr. et al. | |
| 2001/0016210 A1 | 8/2001 | Mathiowitz et al. | |
| 2001/0036451 A1 | 11/2001 | Goupil et al. | |
| 2001/0051670 A1 | 12/2001 | Goupil et al. | |
| 2002/0054912 A1 | 5/2002 | Kim et al. | |
| 2002/0061954 A1 | 5/2002 | Davis et al. | |
| 2002/0160109 A1 | 10/2002 | Yeo et al. | |
| 2002/0182190 A1 | 12/2002 | Naimark et al. | |
| 2002/0197208 A1 | 12/2002 | Ruys et al. | |
| 2003/0007928 A1 | 1/2003 | Gray | |
| 2003/0032935 A1 | 2/2003 | Damiano et al. | |
| 2003/0097120 A1 | 5/2003 | Santerre | |
| 2003/0108614 A1 | 6/2003 | Volkonsky et al. | |
| 2003/0183962 A1 | 10/2003 | Buiser et al. | |
| 2003/0185895 A1 | 10/2003 | Lanphere et al. | |
| 2003/0185896 A1 | 10/2003 | Buiser et al. | |
| 2003/0187320 A1 | 10/2003 | Freyman | |
| 2003/0194390 A1 | 10/2003 | Krall et al. | |
| 2003/0203985 A1 | 10/2003 | Baldwin et al. | |
| 2003/0206864 A1 | 11/2003 | Mangin | |
| 2003/0215519 A1 | 11/2003 | Schwarz et al. | |
| 2003/0233150 A1 | 12/2003 | Bourne et al. | |
| 2004/0076582 A1 | 4/2004 | DiMatteo et al. | |
| 2004/0091543 A1 | 5/2004 | Bell et al. | |
| 2004/0092883 A1 | 5/2004 | Casey, III et al. | |
| 2004/0096662 A1 | 5/2004 | Lanphere et al. | |
| 2004/0101564 A1 | 5/2004 | Rioux et al. | |
| 2004/0186377 A1 | 9/2004 | Zhong et al. | |
| 2005/0025800 A1 | 2/2005 | Tan | |
| 2005/0037047 A1 | 2/2005 | Song | |
| 2005/0095428 A1 | 5/2005 | DiCarlo et al. | |
| 2005/0129775 A1 | 6/2005 | Lanphere et al. | |

FOREIGN PATENT DOCUMENTS

| | | |
|---|---|---|
| DE | 3834705 | 4/1990 |
| DE | 94 14 868 | 2/1995 |
| DE | 297 24 255 | 10/2000 |
| DE | 100 26 620 | 3/2002 |
| EP | 0 067 459 | 12/1982 |
| EP | 0 122 624 | 10/1984 |
| EP | 0 123 235 | 10/1984 |
| EP | 0 243 165 | 10/1987 |
| EP | 0 294 206 | 12/1988 |
| EP | 0 422 258 | 10/1989 |
| EP | 0 402 031 | 5/1990 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 | 12/1993 |
| EP | 0 623 012 | 11/1994 |
| EP | 0 706 376 | 4/1996 |
| EP | 0 730 847 | 9/1996 |
| EP | 0 744 940 | 12/1996 |
| EP | 0 797 988 | 10/1997 |
| EP | 0 067 459 | 3/1998 |
| EP | 0 764 047 | 8/2003 |
| EP | 0 993 337 | 4/2004 |
| EP | 1 742 614 | 5/2009 |
| ES | 2 096 521 | 3/1997 |
| JP | 59-196738 | 11/1984 |
| JP | 62-45637 | 2/1987 |
| JP | 4-74117 | 3/1992 |
| JP | 6-57012 | 3/1994 |
| JP | 9-110678 | 4/1997 |
| JP | 9-165328 | 6/1997 |
| JP | 9-316271 | 12/1997 |
| JP | 10-130329 | 5/1998 |
| JP | 2000189511 | 7/2000 |
| JP | 2001079011 | 3/2001 |
| JP | 2002 017848 | 1/2002 |
| NZ | 255409 | 2/1997 |
| NZ | 517377 | 8/2003 |
| TW | 421658 | 2/2001 |
| WO | WO 91/12823 | 5/1991 |

| | | |
|---|---|---|
| WO | WO 92/21327 | 12/1992 |
| WO | WO 93/00063 | 1/1993 |
| WO | WO 93/19702 | 10/1993 |
| WO | WO 94/10936 | 5/1994 |
| WO | WO 95/03036 | 2/1995 |
| WO | WO 95/22318 | 8/1995 |
| WO | WO 95/33553 | 12/1995 |
| WO | WO 96/37165 | 11/1996 |
| WO | WO 96/39464 | 12/1996 |
| WO | WO 97/06195 | 2/1997 |
| WO | WO 98/04616 | 2/1998 |
| WO | WO 98/10798 | 3/1998 |
| WO | WO 98/26737 | 6/1998 |
| WO | WO 98/47532 | 10/1998 |
| WO | WO 99/00187 | 1/1999 |
| WO | WO 99/12577 | 3/1999 |
| WO | WO 99/43380 | 9/1999 |
| WO | WO 99/51278 | 10/1999 |
| WO | WO 99/57176 | 11/1999 |
| WO | WO 00/23054 | 4/2000 |
| WO | WO 00/32112 | 6/2000 |
| WO | WO 00/40259 | 7/2000 |
| WO | WO 00/71196 | 11/2000 |
| WO | WO 00/74633 | 12/2000 |
| WO | WO 01/12359 | 2/2001 |
| WO | WO 01/66016 | 9/2001 |
| WO | WO 01/70291 | 9/2001 |
| WO | WO 01/72281 | 10/2001 |
| WO | WO 01/76845 | 10/2001 |
| WO | WO 01/93920 | 12/2001 |
| WO | WO 02/11696 | 2/2002 |
| WO | WO 02/34298 | 5/2002 |
| WO | WO 02/34299 | 5/2002 |
| WO | WO 02/34300 | 5/2002 |
| WO | WO 02/43580 | 6/2002 |
| WO | WO 02/098477 | 12/2002 |
| WO | WO 03/013552 | 2/2003 |
| WO | WO 03/016364 | 2/2003 |
| WO | WO 03/051451 | 6/2003 |
| WO | WO 03/082359 | 9/2003 |
| WO | WO 03/082360 | 10/2003 |
| WO | WO 03/084582 | 10/2003 |
| WO | WO 2004/014446 | 2/2004 |
| WO | WO 2004/019999 | 3/2004 |
| WO | WO 2004/020011 | 3/2004 |
| WO | WO 2004/040972 | 5/2004 |
| WO | WO 2004/073688 | 9/2004 |
| WO | WO 2004/075989 | 9/2004 |
| WO | WO 2005/034912 | 4/2005 |
| WO | WO 2005/084645 | 9/2005 |

OTHER PUBLICATIONS

Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.

Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.

Ahuja, A.A., "Platinum Coil Coatings to Increase Thrombogenicity: A Preliminary Study in Rabbits", *AJNR Am. J. Neuroradiol.* 14:794-798; Jul./Aug. 1993.

Antibody Labeling, http://www.altcorp.com/AffinityLabeling/ablaeling.htm, pp. 1-6, May 20, 2003.

Bachtsi, A.R. et al., "An Experimental Investigation of Enzyme Release from Poly(vinyl alcohol) crosslinked Microspheres", *J. Microencapsulation*, vol. 12, No. 1, pp. 23-35; 1995.

Barr, J.D., et al., "polyvinyl Alcohol Foam Particles Sizes and Concentrations Injectable through Microcatheters", *JVIR*, vol. 9, No. 1, pp. 113-118; 1998.

Barton, P. et al., "Embolization f Bone Metastases", *Journal of Vascular and Interventional Radiology*, vol. 7, No. 1, Jan.-Feb. 1996, p. 81-88.

Barttinelli, L. et al., "New Class of Poly(vinyl alcohol) Polymrs as Column—Chromatography Stationary Phases for *Candida rugosa* Lipase Isoforms Separation.", *J. Chromatogr A*, vol. 753, No. 1, pp. 47-55; 1996. Abstract. http://www.ncbi.nlm.nih.gov/entrez/query.fcgi?

Beaujeux, R. et al., "Trisacryl Gelatin Microspheres for Therapeutic Embolization, II: Preliminary Clinical Evaluation in Tumors and Arteriovenous Malformations," *AJNR Am. J. Neuroradiol.* 17:541-548, Mar. 1996.

Berenstein, A. et al., "Catheter and Material Selection for Transarterial Embolization: Technical Considerations. II. Materials.", *Radiology*, vol. 132, No. 3, pp. 631-639; 1979.

Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981. Abstract, http://www.ncbi.nlm.nih.gov/entrez/query.fcgi?

Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.

Bourke et al., "Protein Drug Release from Photocrosslinked Poly(vinyl alcohol) Hydrogels," *Society for Biomaterials 28$^{th}$ Annual Meeting Transactions*, p. 144 (2002).

Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.

Brockmann, J. et al., "Radiolabeling of p-Bz-DOTA-CD-11c antibody with $^{88}$Y: Conjugation, Labeling, Biodistribution studies", 2 pages, 2000 http://www.kernchemie.uni-mainz.de/downloads/jb2000/b14_brockmann.pdf.

Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578-1583 Available Web Site: http://www.hepatitis-central.com/hcv/hcc/embolization/references.html.

Buhle, Jr. EL, "Re: Re: Hepatic Arterial Embolization", *UCLA Medicine Online* Available Web Site: http://www.meds.com/archive/molcancer/1996/msg00128.html.

Burczak, et al., "Long-term in vivo performance and biocompatibility of poly (vinyl alcohol) hydrogel macrocapsules for hybrid-type artificial pancreas", *Biomaterials*, vol. 17, No. 24, pp. 2351-2356, 1996, abs: http://www.ncbi.nlm.nih.gov/entrez/query.fcgi?cmd=retrieve&db=PubMed&list_uids=89824..., pp. 1, 2002.

Burczak, et al., "Polymeric materials for biomedical purposes obtained by radiation methods. V. hybrid artificial pancreas", *Polim Med*, vol. 24, No. 1-2, pp. 45-55, 1994, abs: http://www.ncbi.nlm.nih.gov/entrez/query.fcgi?cmd=retrieve&db=PubMed&list_uids=7915...; pp. 1, 2002.

Capozza et al., "Endoscopic treatment of vesico-ureteric reflux and urinary incontinence: technical problems in the paediatric patient," *British Journal of Urology*, 75(4):538-542 (Apr. 1995).

Carroll, B.A. et al., "Gelatin Encapsulated Nitrogen Microbubbles as Ultrasonic Contrast Agents", *Journal of Clinical and Laboratory Research*, vol. 15, No. 1, pp. 260-266, Feb. 1980.

Carroll, B.A. et al., "Microbubbles as Ultrasonic Contrast Agents", *Investigative Radiology*, vol. 14, No. 3, p. 374, Supplement to May-Jun. 1979.

Carstensen, E.L. et al., "Determination of the Acoustic Properties of Blood and its Components", *Journal of Acoustical Society of America*, vol. 25, No. 2, pp. 286-289, Mar. 1953.

Choe, et al., "An experimental study of embolic effect according to infusion rate and concentration of suspension in transarterial patriculate embolization", *Invest Radiol*, vol. 32, No. 5, pp. 260-270, 1997, abs: http://www.ncbi.nlm.nih.gov/entrez/query.fcgi?cmd=retrieve&db=PubMed&list_uids=9140745&dopt+Abs..., pp. 1, 2002.

Chuang et al., "Experimental Canine Hepatic Artery Embolization with Polyvinyl Alcohol Foam Particles", *Departments of Diagnostic Radiology and Veterinary Medicine*, The University of Texas, M.D. Anderson Hospital and Tumor Institute at Houston, Texas, pp. 21-25.

Cirkel, U. et al., "Experience with Leuprorelin Acetate Depot in the Treatment of Fibroids: A German Multicentre Study", *Clinical Therapeutics*, vol. 14, Suppl. A, 1992.

Clarian Health Methodist—Indiana Lions Gamma Knife Center, "Arteriovenous Malformation" Available Web Site: http://www.clarian.com/tyhealth/gammaknife/cond_arter.asp.

Colombo M, "Treatment of Hepatocellular Carcinoma", University of Milan, Inst Internal Med, Irccs Maggiore Res Unit Liver, Canc, Firc, Via Pace 9 1-20122 Milan, Italy Source: Journal of Viral Hepatitis, 1997;4:125-130 Available Web Site: http://home.texoma.net/~moreland/stats/hcc-9.html.

Concentric Medical, Inc.—Product Information (3 pages), 2002.

Cruise et al., "In Vitro and in Vivo Characterization of a Hydrogel-Based Aneurysm Embolization System," *Society for Biomaterials 28th Annual Meeting Transactions*, p. 203 (2002).

Deasy, P. B., "*Microencapsulation and Related Drug Processes*", New York, NY, Marcel Dekker, Inc., 345 pages, 1984 (Table of Contents only).

DeGast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.

Derdeyn, et al., "Collagen-coated acrylic microspheres for embolotherapy: in vivo and in vitro characteristics", *American Journal of Neuroradiology*, vol. 18, No. 4, pp. 647-653, 1997, abs: http://www.ncbi.nlm.nih.gov/entrez/query.fcgi?cmd=retrieve&db=PubMed&list_uids=9127025&dopt=Abs..., pp. 1, 2002.

Derdeyn, et al., "Polyvinyl alcohol particle size and suspension characteristics", *American Journal of Neuroradiology*, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", *Journal of Pharmaceutical Sciences*, Jan. 1994, vol. 83, No. 1, pp. 104-106.

Duckwiler et al., "Catheters, embolic agents spark neurointervention," *Diagnostic Imaging*, 16(5):66-72 (May 1994).

Ersek et al., "Bioplastique: A New Textured Copolymer Microparticle Promises Permanence in Soft-Tissue Augmentation," *Plastic and Reconstructive Surgery*, 87(4):693-702 (Apr. 1991).

Eskridge, "Interventional Neuroradiology," *Radiology*, 172:991-1006 (Nov. 1989).

Feldman, L. et al., "Transcatheter Vessel Occlusion: Angiographic Results Versus Clinical Success", *Radiology*, vol. 147, pp. 1-5, Apr. 1983.

Ferrofluids, Physical Properties and Applications, Ferrofluidics Corp., Nashua, NH, 5 pages, 1986.

FeRx Incorporated, FERX Profile http://www.biotechshares.com/FERX.htm, 4 pages (Retrieved from the internet on Jun. 26, 2003).

"Fibroid Treatment Collective—Fibroid Embolization," 2 pages, http://www.fibroids.org.

Fritzsch, T. et al., "SH U 508, A Transpulmonary Echocontrast Agent", *Investigative Radiology*, vol. 25, Supplement 1, pp. S160-S161, Sep. 1990.

Fujimoto, S. et al., "Biodegradable Mitomycin C Microspheres Given Intra-Arterially for Inoperable Hepatic Cancer", *Cancer*, vol. 56, pp. 2404-2410, 1985.

Gander, et al., "Effect of polymeric network structure on drug release from cross-linked poly(vinyl alcohol) micromatrices", *Pharm Res*, vol. 6, No. 7, pp. 578-584, 1989, abs: http://www.ncbi.nlm.nih.gov/entrez/query.fcgi$8 cmd=retrieve&db=PubMed&list_uids=25080..., pp. 1, 2002.

Germano, et al., "Histopathological follow-up study of 66 cerebral arteriovenous malformations after therapeutic embolization with polyvinyl alcohol", *J. Neurosurg*, vol. 76, No. 4, pp. 607-614, 1992, abs: http://www.ncbi.nlm.nih.gov/entrez/query.fcgi?cmd=retrieve&db=PubMed&list_uids=15452..., pp. 1, 2002.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, Dec. 2000, vol. 11, No. 10, pp. 1244-1255.

Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.

Gohel, et al., "Formulation design and optimization of modified-release microspheres of diclofenac sodium", *Drug Dev Ind Pharm*, vol. 25, No. 2, pp. 247-251, 1999, abs: http://www.ncbi.nlm.nih.gov/entrez/query.fcgi?cmd=retrieve&db=PubMed&list_uids=10065360&dop=A..., pp. 1, 2002.

Goldberg, B.B., "Ultrasonic Cholangiography", *Radiology*, vol. 118, pp. 401-404, Feb. 1976.

Goodwin, et al., "Overview of embolic agents and their indications", *Eleventh Annual International Symposium on Endovascular Therapy*, pp. 303-306, 1999.

Goodwin, et al., "Preliminary experience with uterine artery embolization for uterine fibroids", *Journal of Vascular and Interventional Radiology*, vol. 8, No. 4, pp. 517-526, 1997.

Gramiak et al., "Echocardiography of the Aortic Root," *Investigative Radiology*, 3(5):356-366 (Sep.-Oct. 1968).

Gramiak, R. et al., "Ultrasound Cardiography: Contrast Studies in Anatomy and Function", *Radiology*, vol. 92, No. 5, pp. 939-948, Apr. 1969.

Grandfils, et al., "Preparation of poly (D,L) lactide microspheres by emulsion solvent evaporation, and their clinical implications as a convenient embolic material", *J Biomed Mater Res*, vol. 26, No. 4, pp. 467-479, 1992, abs: http://www.ncbi.nlm.nih.gov/entrez/query.fcgi?cmd=retrieve&db=PubMed&list_uids=1601900&dopt=Abs..., pp. 1, 2002.

Greenwood, L.H. et al., "Obstetric and Nonmalignant Gynecologic Bleeding: Treatment with Angiographic Embolization", *Radiology*, vol. 164, No. 1, pp. 155-159, Jul. 1987.

Gupta et al., "Plasma-induced graft polymerization of acrylic acid onto poly(ethylene terephthalate) films: characterization and human smooth muscle cell growth on grafted films," *Biomaterials*, 23:863-871 (2002).

Halstenberg et al., "Biologically Engineered Protein-*graft*-Poly(ethylene glycol) Hydrogels: A Cell Adhesive and Plasmin-Degradable Biosynthetic Material for Tissue Repair," *Biomacromolecules*, 3(4):710-723 (2002).

Hamada, et al., "Embolization with cellulose porous beads, II: Clinical Trial", abs: http://www.ajnr.org/content/abstract/17/10/1901?ijkey=R.a2vRMiet1Xw, pp. 1-2, 2002.

Hirano et al., "Transcutaneous Intrafold Injection for Unilateral Vocal Fold Paralysis: Functional Results," *Ann. Otol. Rhinol Laryngol.*, 99(8):598-604 (Aug. 1990).

Horak, et al., "Hydrogels in endovascular embolization. I. Spherical particles of poly (2-hydroxyethyl methacrylate) and their medico-biological properties".

Horak, et al., "Hydrogels in endovascular embolization. II. Clinical use of spherical particles", *Biomaterials*, vol. 7, 1986.

Huang, et al., "Percutaneous endovascular embolization of intracerebral arteriovenous malformations. Experience in 72 cases", *Chin Med J*, vol. 108, No. 6, pp. 413-419, 1995, abs: http://www.ncbi.nlm.nih.gov/entrez/query.fcgi?cmd=retrieve&db=PubMed&list_uids=75552..., pp. 1, 2002.

"Injectable Tissue Implant Could Repair Ravages of Surgery", Clemson University, Biotech Week, Oct. 22, 2003, p. 117.

International Search Report and Written Opinion, PCT/US2005/006411, mailed Jul. 5, 2005.

International Search Report for International Application No. PCT/US01/06981 (2 pages).

Jack, et al., "Radiolabeled polyvinyl alcohol particles: a potential agent to monitor embolization procedures", *Int J Rad Appl Instrum B*, vol. 13, No. 3, pp. 235-243, 1986, abs: http://www.ncbi.nlm.nih.gov/entrez/query.fcgi?cmd=retrieve&db=PubMed&list_uids=37712, pp. 1, 2002.

Jiaqi, Y. et al., "A New Embolic Material: Super Absorbent Polymer (SAP) Microsphere and Its Embolic Effects," *Nippon Acta Radiologica* 1996 (56): 19-24.

Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001, www.iop.org/Journals/pb.

Joy C, et al., 1991, "Use of Preoperative Embolization in the Treatment of Vascular Metastatic Lesions of the Spine" Available Web Site: http://www.aaos.org/wordhtml/anmeet91/scipro/ppr472.htm.

Jung et al., "Sulfobutylated poly(vinyl alcohol)-graft-poly(lactide-co-glycolide)s facilitate the preparation of small negatively charged biodegradable nanospheres," *Journal of Controlled Release*, 67:157-169 (2000).

Kai, et al., "The utility of the microcrystalline cellulose sphere as a particulate embolic agent: an experimental study", *American Journal of Radiology*, vol. 21, No. 6, pp. 1160-1163, 2000, or http://www.ajnr.org/cgi/content/full/21/6/1160, pp. 1-7, 2002.

Kallmes, D.F. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.

Kan, et al., "In vivo microscopy of the liver after injection of lipiodol into the hepatic artery and portal vein in the rat", *Acta Radiologica*, vol. 30, pp. 419-425, 1989.

Kerber et al., "Polyvinyl Alcohol Foam: Prepackaged Emboli for Therapeutic Embolization", *American Journal Roentgenol*, Jun. 1978, vol. 130, pp. 1193-1194.

Kerber, "Flow-Controlled Therapeutic Embolization: A Physiologic and Safe Technique", *AJR*, Mar. 1980, vol. 134, pp. 557-561.

Kerber, C., "Balloon Catheter with a Calibrated Leak", *Radiology*, vol. 120, pp. 547-550, Sep. 1976.

Khankan et al., "Embolic Effects of Superabsorbent Polymer Microspheres in Rabbit Renal Model: Comparison with Tris-acryl Gelatin Microspheres and Polyvinyl Alcohol," *Radiation Medicine*, 22(6):384-390 (2004).

Kim et al., "Hollow Silica Spheres of Controlled Size and Porosity by Sol-Gel Processing," *J. Am. Ceram. Soc.*, 74(8):1987-1992 (Aug. 1991).

Kim et al., "Poly(vinyl alcohol) beads with core-shell structure for drug delivery," *Cosmetic and Pharmaceutical Applications of Polymers*, Plenum Press, New York, pp. 209-214 (1991).

Kim et al., "Suspension polymerized poly(vinyl alcohol) beads for drug delivery," *Polymeric Materials: Science and Engineering, Proceedings of the ACS Division of Polymeric Materials: Science and Engineering*, 63:64-67 (1990).

Kim, et al., "Composite poly(vinyl alcohol) beads for controlled drug delivery", *Pharm Res*, vol. 9. No. 1, pp. 10-16, 1992, abs: http://www.ncbi.nlm.nih.gov/entrez/query.fcgi?cmd=retrieve&db=PubMed&list_uids=1589392&dopt=Abs..., pp. 1, 2002.

Kochan, J.P. et al., "Interventional Neuroradiology: Current Practices and Techniques at Temple University Hospital," http://www.temple.edu/radiology/stroke.html, 5 pages.

Krinick et al., "A polymeric drug delivery system for the simultaneous delivery of drugs activatable by enzymes and/or light," *J. Biomater. Sci. Polymer Edn*, 5(4):303-324 (1994).

Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.

Kurata, et al., "Preoperative embolization for meningiomas using PVA particles", *No Shinkei Geka*, vol. 20, No. 4, pp. 367-373, 1992, abs: http://www.ncbi.nlm.nih.gov/entrez/query.fcgi?cmd=retrieve&db=PubMed&list_uids=1570057&dopt=Abs..., pp. 1, 2002.

Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp.

Kurosaki et al., "Evaluation of PVA-Gel Spheres as GI-Transit Time Controlling Oral Drug Delivery System", *Proceedings of the 19th International Symposium on Controlled Release of Bioactive Materials*, Jul. 26-31, 1992, Orlando, Florida, pp. 273-274.

Kusano, et al., "Low-dose particulate polyvinylalcohol embolization in massive small artery intenstinal hemorrahage. Experimental and clinical results", *Invest Radiol*, vol. 22, No. 5, pp. 388-392, 1987, abs: http://www.ncbi.nlm.nih.gov/entrez/query.fcgi?cmd=retrieve&db=PubMed&list_uids=34963..., pp. 1, 2002.

Labarre et al., "Complement activation by substituted polyacrylamide hydrogels for embolisation and implantation", *Biomaterials*, vol. 23, pp. 2319-2327, 2002.

Lammer, et al., "Transcatheteral embolization with polyvinyl alcohol—technic and experimental studies", *Rontgenblatter*, vol. 36, No. 1, pp. 10-14, 1983, abs: http://www.ncbi.nlm.nih.gov/entrez/query.fcgi?cmd=retrieve&db=PubMed&list_uids=6823530&dop=Abs..., pp. 1, 2002.

Latchaw et al., "Polyvinyl Foam Embolization of Vascular and Neoplastic Lesions of the Head, Neck, and Spine", *Radiology*, Jun. 1979, vol. 131, pp. 669-679.

Laurent, "Materials and biomaterials for interventional radiology," *Biomed. & Pharmacother.*, 52:76-88 (1998).

Lemperle et al., "PMMA Microspheres for Intradermal Implantation: Part I. Animal Research," *Annals of Plastic Surgery*, 26(1):56-63 (Jan. 1991).

Lendlein, A. et al., "Biodegradable, Elastic Shape-Memory Polymers for Potential Biomedical Applications", *Science*, vol. 296, pp. 1673-1676, May 31, 2002.

Leung et al., "Determinants of Postembolization Syndrome after Hepatic Chemoembolization", *Journal of Vascular and Interventional Radiology*, Mar. 2001, vol. 12, No. 3, pp. 320-326.

Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.

Levy et al., "Transcatheter Uterine Artery Embolization for the Treatment of Symptomatic Uterine Fibroid Tumors," *Journal of Women's Imaging*, 2(4):168-175 (2000).

Lipman, "Uterine artery embolization for the treatment of symptomatic uterine fibroids: A review," *Applied Radiology*, 29(7):15-20 (Jul. 2000).

Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.

Markoff, et al., "Uterine arteriovenous malformation successfully embolized with a liquid polymer, isobutyl 2-cyanoacrylate", pp. 659-660, 1999.

Markus, H.S., "Experimental Aspects of High-Intensity Transient Signals in the Detection of Emboli," *J Clin Ultrasound* 23:81-87 (1995).

Maruhashi, "Modified Polyvinyl Alcohols I and II," *Polyvinyl Alcohol—Developments*, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.

Mather, P.T., Research Group Homepage, Basic Goals and Methods, http://www.ims.uconn.edu/~mather, 4 pages.

Matsumaru, et al., "Embolic materials for endovascular treatment of cerebral lesions", *J Biomater Sci Polym Ed*, vol. 8, No. 7, pp. 555-569, 1997, abs: http://www.ncbi.nlm.nih.gov/entrez/query.fcgi?cmd=retrieve&db=PubMed&list_uids=91953..., pp. 1, 2002.

Matsumoto, H. et al., "Basic Fibroblast Growth Factor Released from a Platinum Coil with a Polyvinyl Alcohol Core Enhances Cellular Proliferation and Vascular Wall Thickness: An in Vitro and in Vivo Study", *Neurosurgery*, vol. 53, No. 2, pp. 402-408, Aug. 2003.

Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.

Mavligit, G. et al., "Gastrointestinal Leiomyosarcoma Metastatic to the Liver," *Cancer*, vol. 75, No. 8, Apr. 15, 1995, pp. 2083-2088.

McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.

MerocelXL Sponge with Hytrol http://www.xomed.com/newproducts/merocelxl/merocelxl_earwick.asp, 3 pages, 2001.

Mid-America Interventional Radiological Society, "New Treatment for Uterine Fibroids Avoids Surgery" Available Web Site: http://www.mirs.org/fibroids.htm.

Moroz, P. et al., "Arterial Embolization Hyperthermia in Porcine Renal Tissue", *Journal of Surgical Research*, vol. 105, No. 2, pp. 209-214, Jun. 15, 2002.

Moroz, P. et al., "Hepatic Clearance of Arterially Infused Ferromagnetic Particles", *Int. J. Hyperthermia*, vol. 19, No. 1, pp. 23-24, Feb. 2003, http://www.tandf.co.uk/journals.

Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997, abs: http://www.ncbi.nlm.nih.gov/entrez/query.fcgi?cmd=retrieve&db=PubMed&list_uids=909004..., pp. 1, 2002.

Nakstad, et al., "Embolization of intracranial arteriovenous malformations and fistulas with polyvinyl alcohol particles nad platinum fibre coils", *Neuroradiology*, vol. 34, No. 4, pp. 348-351, 1992, abs: http://www.ncbi.nlm.nih.gov/entrez/query.fcgi?cmd=retrieve&db=PubMed&list_uids=152854..., pp. 1, 2002.

Namiki, "Application of Teflon Paste for Urinary Incontinence—Report of 2 Cases," *Uro. Int.*, 39:280-282 (1984).

Nash, et al., "Modifications of polystyrenic matrices for the purification of proteins. II. Effect of the degree of glutaraldehyde-poly(vinyl alcohol) crosslinking on various dye ligand chromatography systems", *J Chromatogr A*, vol. 776, No. 1, pp. 55-63, 1997, abs: http://www.ncbi.nlm.nih.gov/entrez/query.fcgi?cmd=retrieve&db=PubMed&list_uids=92860..., pp. 1, 2002.

Nikishin LF et al., 1999, "Interventional radiology in diffuse toxic goiter", Euro*pean Congress of Radiology—ECR* 1999 Available Web Site: http://www.ecr.org/conferences/ecr1999/sciprg/abs/p090041.htm.

Ophir, et al., "Ultrasonic backscatter from contrast producing collagen microspheres", *Ultrasonic Imaging*, vol. 2, pp. 67-77, 1980.

Oregon Health Sciences University, "Fibroid Embolization" Available Web Site: http://www.uhmc.edu/dotter-fibroid.

Orienti et al., "Crosslinked Polyvinylalcohol Hydrogels as Vehicles for Hydrophilic Drugs," *Arch. Pharm. Pharm. Med. Chem.*, 333:421-424 (2000).

Orsini, L. F. et al., "Pelvic Organs in Premenarcheal Girls: Real-Time Ultrasonography", *Radiology*, vol. 153, No. 1, pp. 113-116, Oct. 1984.

Parker, et al., "A particulate contrast agent with potential for ultrasound imaging of liver", *Ultrasound in Medicine and Biology*, vol. 13, No. 9, pp. 555-566, 1987.

Pedley et al., "Hydrogels in Biomedical Applications," *British Polymer Journal*, 12:99-110 (Sep. 1980).

Pesant A.C. et al., 1997, "Dural fistulas involving the cavernous sinus: Treatment by embolization—7 cases", *European Congress of Radiology—ECR* 1997 Available Web Site: http://www.ecr.org/conferences/ecr1997/sciprg/abs/9703088p.htm.

Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.

Physicians' Desk Reference Family Guide to Women's Health, "Chapter 7—Common Disorders of the Reproductive System" Available Web Site: http://www.healthsquare.com/pdrfg/wh/chapters/wh1ch01.htm.

Pistel et al., "Brush-like branched biodegradable polyesters, part III Protein release from microspheres of poly(vinyl alcohol)-graft-poly(D,L-lactic-co-glycolic acid)," *Journal of Controlled Release*, 73:7-20 (2001).

Politano et al., "Periurethral Teflon Injection for Urinary Incontinence," *The Journal of Urology*, 111:180-183 (1974).

Poppe, W. et al., "Pregnancy after Transcatheter Embolization of a Uterine Arteriovenous Malformation", *Am. J Obstet. Gynecol.*, vol. 156, No. 5, pp. 1179-1180, May 1987.

Pritchard, et al., "*Poly(Vinyl Alcohol): Basic Properties and Uses*", London, England: Gordon and Breach Science Publishers.

Progelhof et al., "Table 4.21. Properties of electrical insulating films (101),"*Polymer Engineering Principles: Properties, Processes, and Tests for Design*, Hanser Publishers, Munich, p. 383 (1993).

Pryor J and Berenstein A., "Epistaxis (Nose-bleeds)" Available Web Site: http://www.wehealny.org/inn/Radiology/nosebleeds.html.

Purdy, et al., "Arteriovenous malformations of the brain: choosing embolic materials to enhance safety and ease of excision", *J Neurosurg*, vol. 77, No. 2, pp. 217-222, 1992, abs: http://www.ncbi.nlm.nih.gov/entrez/query.fcgi?cmd=retrieve&db=PubMed&list_uids=16250..., pp. 1, 2002.

"Pulmonary artery pseudoaneuyrsm/aneurysm" Available Web Site: http://www.mamc.amedd.army.mil/williams/chest/vascular/paaneurysm/paaneyrysm.htm.

PVA Plus, AngioDynamics® Inc., "Reliable PVA Foam Formulated for Consistency and Controlled Delivery—Embolization Particles Ordering Information," www.angiodynamics.com, 2 pages (Aug. 2002).

Quisling, et al., "Histopathology analysis of intraarterial polyvinyl alcohol microemboli in rat cerebral cortex", *American Journal of Neuroradiology*, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, Feb. 2001, vol. 12, No. 2, pp. 187-193.

Ramos, et al., "Tumor vascular signals in renal masses: detection with Doppler US", *Radiology*, vol. 168, No. 3, pp. 633-637, 1988.

Ravina, J.H. et al., "Advantage of Pre-Operative Embolization of Fibroids: About a Multicentric Set of 31 Cases", *Contracep. Fertil. Sex.*, vol. 23, No. 1, pp. 45-49, Jan. 1995 (abstract).

Ravina, J.H. et al., "Arterial Embolisation to Treat Uterine Myomata", *Lancet*, vol. 346, pp. 671-674, Sep. 9, 1995.

Ravina, J.H. et al., "Interest of Particulate Arterial Embolization in the Treatment of Some Uterine Myoma", *Bull. Acad. Natle. Med.*, vol. 181, No. 2, pp. 233-246, Feb. 4, 1997 (Summary).

Repa, I. et al., "Mortalities Associated with Use of a Commercial Suspension of Polyvinyl Alcohol", *Radiology* 1989; 170:395-399.

Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).

Rump, A. et al., "Pharmacokinetics of Intraarterial Mitomycin C in the Chemoembolisation Treatment of Liver Metastases", *Gen. Pharmac.* vol. 27, No. 4, pp. 669-671, 1996.

Schetky, "Shape-Memory Alloys," *Encyclopedia of Chemical Technology*, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.

Schwarz, K.Q., "The Acoustic Filter: An Ultrasonic Blood Filter for the Heart-Lung Machine," *Journal of Thoracic and Cardiovascular Surgery* 104(6):1647-1653 (1992).

Shafik, "Intraesophageal Polytef injection for the treatment of reflux esophagitis," *Surg. Endosc.*, 10:329-331 (1996).

Shafik, A., "Intraesophageal Polytef injection for the treatment of reflux esophagitis", *Department of Surgery and Experimental Research, Faculty of Medicine, Cairo University*, Cairo, Egypt, pp. 1-2, Received: Jun. 22, 1994; Accepted: Oct. 15, 1994 http://ahmedshafik.org/Group-D/d016.htm.

Shape Shifters, http://www.sciam.com/tehbiz/0501scicit6.html, 3 pages, 2001.

Shung, K.K. et al., "Scattering of Ultrasound by Blood", *IEEE Transactions on Biomedical Engineering*, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.

SIR-Spheres (Yttrium-90 Microspheres), pp. 1-12.

SIR-Spheres, Radioactive Implant (Yttrium-90 Microspheres), Sirex Medical, Inc., San Diego, CA, Nov. 6, 2000, pp. 1-15.

Sirtex Medical Limited—Product Description http://www.sirtex.com/?p=72, 3 pages (Retrieved from the internet on May 27, 2003).

Sirtex Medical Limited—Targeted Radiotherapy with SIR-Spheres http://www.sirtex.com/?p=57, 2 pages (Retrieved from the internet on May 27, 2003).

Siskin et al., "Pathologic Evaluation of a Spherical Polyvinyl Alcohol Embolic Agent in a Porcine Renal Model," *J. Vasc. Interv. Radiol.*, 14:89-98 (2003).

Skotland, T. et al., "In Vitro Stability Analyses as a Model for Metabolism of Ferromagnetic Particles (Clariscan™), a Contrast Agent for Magnetic Resonance Imaging", *J. Pharm. Biomed. Anal.*, vol. 28, No. 2, pp. 323-329, Apr. 15, 2002.

"Smart Sutures Tie Themselves", Apr. 26, 2002, http://www.sciam.com/article.cfm?articleID=00047706-121-F-1CD0-B4A8809EC588, 2 pages.

Smith et al., "Evaluation of Polydimethylsiloxane as an alternative in the Endoscopic Treatment of Vesicoureteral Reflux," *The Journal of Urology*, 152:1221-1224 (Oct. 1994).

Smith, M.D. et al., "Left Heart Opacification with Peripheral Venous Injection of a New Saccharide Echo Contrast Agent in Dogs", *JACC*, vol. 13, No. 7, pp. 1622-1628, Jun. 1989.

Soppimath et al., "Controlled release of antihypertensive drug from the interpenetrating network poly(vinyl alcohol)-guar gum hydrogel microspheres," *J. Biomater. Sci. Polymer Edn*, 11(1):27-43 (2000).

Spickler, et al., "The MR appearance of endovascular embolic agents in vitro with clinical correlation", *Comput Med Imaging Graph*, vol. 14, No. 6, pp. 415-423, 1990, abs: http://www.ncbi.nlm.nih.gov/entrez/query.fcgi?cmd=retrieve&db=PubMed&list_uids=21487..., pp. 1, 2002.

Spies JB, "Georgetown University Medical Center. Uterine Fibroid Embolization (UFE). An alternative to surgery for patients with uterine fibroids. Literature Review." Available Web Site: http://www.dml.georgetown.edu/fibroids.

Stancato-Pasik, A. et al., "Obstetric Embolotherapy: Effect on Menses and Pregnancy", *Radiology*, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).

Strasnick et al., "Transcutaneous Teflon® Injection for Unilateral Vocal Cord Paralysis: An Update," *The Laryngoscope*, 101:785-787 (Jul. 1991).

Stridbeck, H. et al, "Collateral Circulation Following Repeated Distal Embolization of the Hepatic Artery in Pigs," *Invest. Radiol.* 1984; 19:179-183.

Strunk, et al., "Treatment of congenital coronary arteriovenous malformations with microparticle embolization", *Cathet Cardiovasc Diagn*, vol. 22, No. 2, pp. 133-136, 1991, abs: http://www.ncbi.nlm.nih.gov/entrez/query.fcgi?cmd=retrieve&db=PubMed&list_uids=2009563&dop=Abs..., pp. 1, 2002.

Swanson DA et al., 1980, "The role of embolization and nephrectomy in the treatment of metastatic renal carcinoma", Urologic Clinics of North America 7(3):719-730, 1980. University of Pennsylvania Cancer Center—Oncolink. Available Web Site: http://www.oncolink.upenn.edu/pdg_html/cites/00/00585.html.

Tabata et al., "Tumor accumulation of poly(vinyl alcohol) of different sizes after intravenous injection", *Journal of Controlled Release*, Jan. 2, 1998, vol. 50, Nos. 1-3, pp. 123-133.

Tadavarthy et al., "Polyvinyl Alcohol (Ivalon) as an Embolizing Agent", *The American Journal of Roentgenology Radium Therapy and Nuclear Medicine*, Nov. 1975, vol. 125, No. 3, pp. 609-616.

Tadavarthy et al., "Polyvinyl Alcohol (Ivalon) as an Embolizing Agent", *Seminars in Interventional Radiology*, vol. 1, No. 2, Department of Radiology, University of Minnesota Hospitals, Minneapolis, Minnesota, Jun. 1984, pp. 101-109.

Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.

Tao, et al., "Study of microspheres for embolization of the hepatic artery", *Yao Xue Xue Bao*, vol. 23, No. 1, pp. 55-60, 1988, abs: http://www.ncbi.nlm.nih.gov/entrez/query.fcgi?cmd=retrieve&db=PubMed&list_uids=3400477&dop=A, pp. 1, 2002.

Tao, et al., "Study on embolization of hepatitic artery using microspheres", Acta Pharmaceutica Sinica vol. 23, No. 1, pp. 55-60; 1988. Translation.

Terada, et al., "Preoperative embolization of meningiomas fed by ophthalmic branch arteries", *Surg Neurol*, vol. 45, No. 2, pp. 161-166, 1996, abs: http://www.ncbi.nlm.nih.gov/entrez/query.fcgi?cmd=retrieve&db=PubMed&list_uids=86070..., pp. 1, 2002.

Thanoo, et al., "Controlled release of oral drugs from cross-linked polyvinyl alcohol microspheres", *J Pharm Pharmacol*, vol. 45, No. 1, pp. 16-20, 1993, abs: http://www.ncbi.nlm.nih.gov/entrez/query.fcgi?cmd=retrieve&db=PubMed&list_uids=8094438&dop=Abs..., pp. 1, 2002.

Thanoo, et al., "Preparation and Properties of Barium Sulphate and Methyl Iothalamate Loaded Poly(vinyl Alcohol) Microspheres as Radiopaque Particulate Emboli", *Journal of Applied Biomaterials*, vol. 2, 67-72 (1991).

Thanoo, et al., "Tantalum loaded silicone micropsheres as particulate emboli", *J Microencapsul*, vol. 8, No. 1, pp. 95-101, 1991, abs: http://www.ncbi.nlm.nih.gov/entrez/query.fcgi?cmd=retrieve&db=PubMed&list_uids=1880697&dop=Abs..., pp. 1, 2002.

The Fibroid Embolization Center of the New York United Hospital Medical Center, "Fibroid Facts" Available Web Site: http://www.uhmc.com/fibro2.htm.

The Vanderbilt-Ingram Cancer Center, "Kidney Cancer." Available Web Site: http://www.mc.Vanderbilt.Edu/cancer/cancerinfo/kidney.html.

Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976.

Tian et al., "Design and synthesis of amphiphilic poly (ethylene glycol) derivatives as micellar drug delivery systems," *Polymer Preprints*, 43(2):719-720 (Fall 2002).

Tikkakoski, et al., "Preoperative embolization in the management of neck paragangliomas", *Laryngoscope*, vol. 107, pp. 821-826, 1997.

Toon, "Improving a Key Weapon Against Cancer," Research Horizons, pp. 11-12, Spring/Summer 2001.

Touho, et al., "Intravascular treatment of spinal arteriovenous malformaitons using a microcatheter—with special reference to serial xylocaine tests and intravascular pressure monitoring", *Surgical Neurology*, vol. 42, No. 2, pp. 148-156. 1994, abs: http://www.ncbi.nlm.nih.gov/entrez/query.fcgi?cmd=retrieve&db=PubMed&list_uids=80912..., pp. 1, 2002.

UCLA Radiological Sciences, "A summary of terms appearing in this text." Available Web Site: http://www.radsci.ucla.edu:8000/aneurysm/terms.html.

University Medical Center SUNY Stony Brook, Department of Urology, "Variococele and its treatment." Available Web Site: http://www.hsc.sunysb.edu/urology/male_inf...variocoele_and_its_treatment.html.

Vivas S et al., "Arterioportal fistula and hemobilia in a patient with hepatic transplant", Gastroenterol Hepatol, Feb. 1998;21(2):88-9 Available Web Site: http://www.doyma.es/copiani/revistas/gastro/abstr/abs_p080.html.

Vogel F, "Nonsurgical Management of Uterine Fibroids" Available Web Site: http://www.holyname.org/brochure/fibroids.html.

Wakhloo, et al., "Extended preoperative polyvinyl alcohol microembolization of intracranial meningiomas: Assessment of two embolization techniques", *American Journal of Neuroradiology*, vol. 14, pp. 571-582, 1993.

Walker WJ, "Non Surgical Treatment of Fibroids in the UK by Uterine Artery Embolisation—An Alternative to Hysterectomy, Myomectomy and Myolysis" Available Web Site: http://www.fibroids.co.uk/thepaper.html.

Walsh RM et al., 1998, "Role of Angiography and Embolization for Acute Massive Upper Gastronintestinal Hemorrhage." Department of General Surgery and Radiology, Cleveland Clinic Foundation, Cleveland, Ohio. Available Web Site: http://www.ssat.com/98ddw/abstscorrt-47.html.

Waltman, A.C. et al., "Technique for Left Gastric Artery Catheterization", *Radiology*, vol. 109, No. 3, pp. 732-734, Dec. 1973.

White, Jr., "Embolotherapy in Vascular Disease," *American Journal of Roentgenology*, 142:27-30 (Jan. 1984).

Widder, K. et al., "Magnetic Microspheres: Synthesis of a Novel Parenteral Drug Carrier", *Journal of Pharmaceutical Sciences*, vol. 68, No. 1, pp. 79-82, Jan. 1979.

Widder, K.J. et al., "Selective Targeting of Magnetic Microspheres Containing Adriamycin: Total Remission in Yoshida Sarcoma-Bearing Rats", *Proceedings of the 16$^{th}$ Annual Meeting of American Society of Clinical Oncology*, May 26-27, 1980, San Diego, CA, p. 261.

Wikholm G et al., 1996, "Embolization of Cerebral Arteriovenous Malformations: Part I—Technique, Morphology, and Complications", Departments of Neurology (CL) and Interventional Radiology (GW, PS), Sahlgrenska University Hospital, Goteborg, Sweden. Neurosurgery. Sep. 1996;39(3):448-57; discussion 457-9. Available Web Site: http://www.wwilkins.com/neurosurgery/0148-396X9-96inter.html.

Winters et al., "Periurethral injection of collagen in the treatment of intrinsic sphincteric deficiency in the female patient," *The Urologic Clinics of North America*, 22(3):673-678 (Aug. 1995).

Worthington-Kirsch RL, 1999, "Interventionalists offer management option for uterine fibroids." Diagnostic Imaging, pp. 47-49. Available Web Site: http://www.dimag.com/reference/9903wortrefs.html.

Worthington-Kirsch, et al., "Uterine arterial embolization for the management of leiomyomas: Quality-of-life assessment and clinical response", *Radiology*, vol. 208, No. 3, 625-629, 1998.

Wright, K.D. et al., "Partial Splenic Embolization Using Polyvinyl Alcohol Foam, Dextran, Polystyrene, or Silicone," *Radiology* 142:351-354, Feb. 1982.

Wu, A.M., "Engineered Antibodies for Breast Cancer Imaging and Therapy," http://www.cbcrp.org/research/PageGrant.asp?grant_id=111, 3 pages, 1996.

Yamada, et al., "Extended intraarterial cisplatin infusion for treatment of gynecological cancer after alteration of intrapelvic blood flow and implantation of a vascular access device", *International Radiology*.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

Yoon et al., "Surface Immobilization of Galactose onto Aliphatic Biodegradable Polymers for Hepatocyte Culture," *Biotechnol. Bioeng.*, 78(1):1-10 (Apr. 5, 2002).

Yusi et al., "Submuscosal Injection of Polyvinyl Alcohol in Artificially Created Vesico-Ureteral Reflux: A Preliminary Report," Asian J. Surg. 18(2): 122-127 (Apr. 1995).

Zisch et al., "Covalently conjugated VEGF-fibrin matrices for endothelialization," *Journal of Controlled Release*, 72:101-113 (2001).

Ziskin, M.C. et al., "Contrast Agents for Diagnostic Ultrasound", *Investigative Radiology*, vol. 7, No. 6, pp. 500-505, Nov.-Dec. 1972.

Zou, Ying-hua et al., "Experimental Canine Hapatic Artery Embolization with Polyvinyl Alcohol Microspheres", *Zong Hua Fang-She Xue ZaZhi*, Dec. 23, 1989 (6): 330-332.

Zou, Ying-hua et al., "Experimental Canine Hapatic Artery Embolization with Polyvinyl Alcohol Microspheres", (Translation) *Zong Hua Fang-She Xue ZaZhi*, Dec. 23, 1989 (6): 330-332.

* cited by examiner

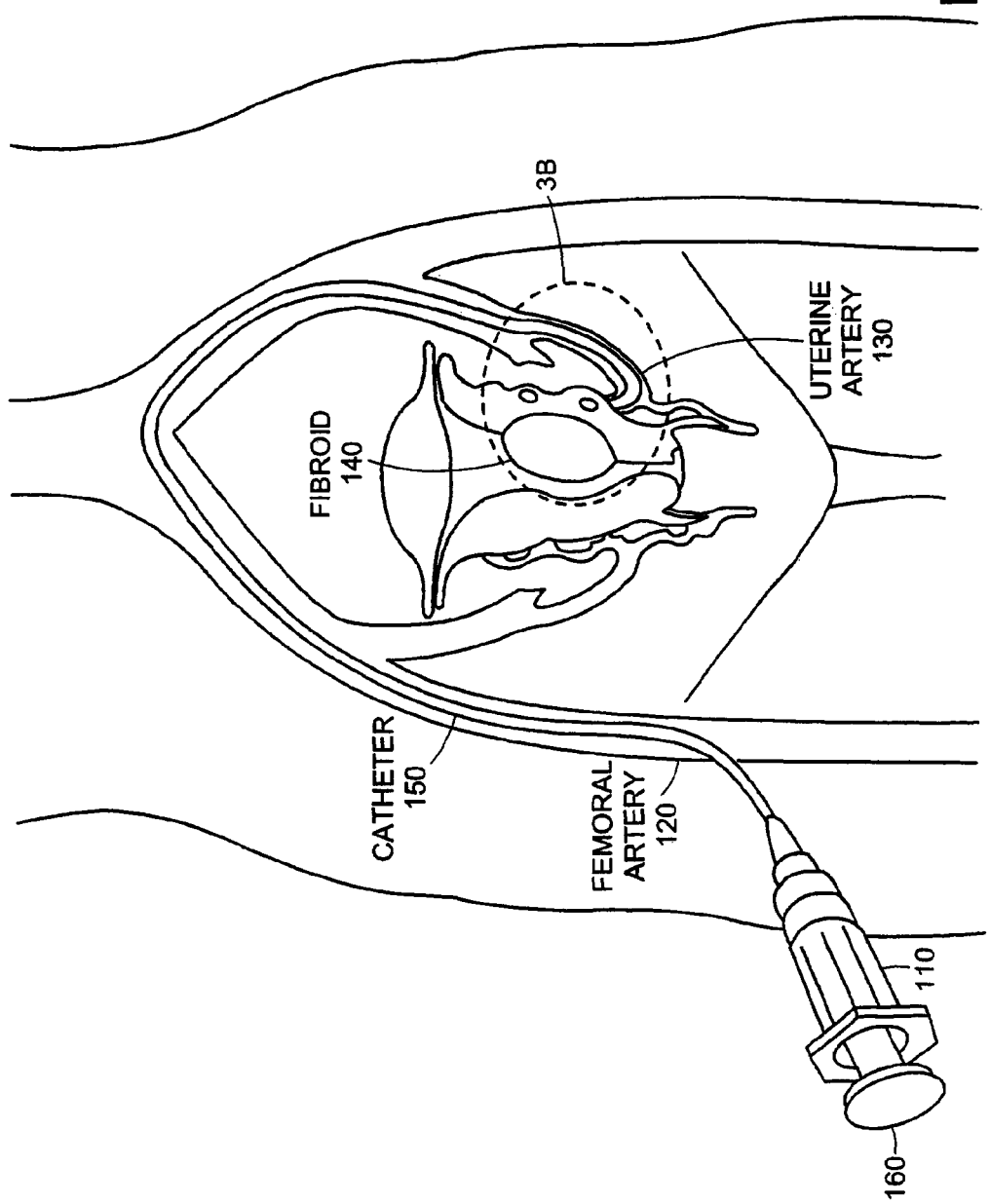

EMBOLIZATION

CROSS-REFERENCE TO RELATED APPLICATIONS

This application is a continuation of and claims the benefit of priority under 35 U.S.C. 120 to U.S. application Ser. No. 10/791,552, filed Mar. 2, 2004, the entire contents of which are being hereby fully incorporated by reference.

TECHNICAL FIELD

The invention relates to embolization, as well as related particles, compositions, and methods.

BACKGROUND

Therapeutic vascular occlusions (embolizations) are used to prevent or treat pathological conditions in situ. Compositions including embolic particles are used for occluding vessels in a variety of medical applications. Delivery of embolic particles through a catheter is dependent on size uniformity, density and compressibility of the embolic particles.

SUMMARY

In one aspect, the invention features a particle that includes a first polymer and that has a diameter of from about ten microns to about 3,000 microns. The particle has an interior region and a surface region, and the surface region of the particle has a higher weight percent of the first polymer than the interior region.

In another aspect, the invention features a composition that includes particles in a carrier fluid. At least some of the particles have a diameter of from about ten microns to about 3,000 microns. At least some of the particles that have a diameter of from about ten microns to about 3,000 microns include a first polymer and have an interior region and a surface region, the interior region having a lower weight percent of the first polymer than the surface region.

In a further aspect, the invention features a method of manufacturing embolic particles. The method includes forming a mixture that contains a first polymer and a gelling compound. The method also includes treating the mixture to form a particle with a diameter of from about ten microns to about 3,000 microns. The particle has an interior region and a surface region, and the interior region has a lower weight percent of the first polymer than the surface region.

In another aspect, the invention features a method that includes administering to a patient a therapeutically effective amount of embolic particles. The embolic particles have a diameter of from about ten microns to about 3,000 microns and include a first polymer. The embolic particles also have an interior region and a surface region, and the interior region has a lower weight percent of the first polymer than the surface region.

Embodiments may also include one or more of the following.

The interior region can be substantially devoid of the first polymer.

The interior region can include at most about 50 weight percent (e.g., at most about ten weight percent) of the first polymer, and/or at least about 0.1 weight percent (e.g., at least about one weight percent) of the first polymer.

The surface region can include at least about 0.1 weight percent (e.g., at least about 25 weight percent) of the first polymer, and/or at most about 100 weight percent (e.g., at most about 75 weight percent) of the first polymer.

The difference between the weight percent of the first polymer in the interior region and the weight percent of the first polymer at the surface region can be at least about 30 weight percent (e.g., at least about 40 weight percent).

The particle can include from about 0.1 weight percent to about 90 weight percent (e.g., from about ten weight percent to about 80 weight percent, from about 25 weight percent to about 85 weight percent, from about 0.25 weight percent to about 50 weight percent, from about 15 weight percent to about 35 weight percent) of the first polymer.

The particle can have a diameter of at least about 100 microns (e.g., at least about 500 microns; at least about 1,000 microns; at least about 1,500 microns; at least about 2,000 microns), and/or at most about 2,500 microns (e.g., at most about 2,000 microns; at most about 1,500 microns; at most about 1,200 microns; at most about 1,000 microns; at most about 500 microns). The particle can have a diameter of from about 100 microns to about 500 microns or a diameter of from about 500 microns to about 1,200 microns.

The particles can have an arithmetic mean diameter of about 3,000 microns or less and/or about ten microns or more.

The first polymer can have the formula D-B-[O-(A-O)$_n$-B]$_m$-D, in which O is a first oligomeric segment, B is a first coupling segment, A is a second coupling segment, D is a polyfluoro oligomeric group, m is from one to 20 (e.g., from one to ten), and n is from zero to 20 (e.g., from two to ten).

O can be a polyurethane, a polyurea, a polyamide, a polyalkylene oxide, a polycarbonate, a polyester, a polylactone, a polysilicone, a polyethersulfone, a polyolefin, a polyvinyl, a polypeptide polysaccharide, or an ether and amine linked segment thereof.

A can be a diamine, a diisocyanate, a disulfonic acid, a dicarboxylic acid, a diacid chloride, or a dialdehyde.

B can be a diamine, a diisocyanate, a disulfonic acid, a dicarboxylic acid, a diacid chloride, or a dialdehyde. B can include a functional group (e.g., an ester, a carboxylic acid salt, a sulfonic acid salt, a phosphonic acid salt, a thiol, a vinyl, a secondary amine).

D can be $CF_3(CF_2)_pCH_2CH_2$—, in which p is from two to 20.

D can be $CF_3(CF_2)_m(CH_2CH_{20})_q$—, in which q is from one to ten and m is from one to 20.

D can be $C_8F_{17}CH_2CH_2$—.

The first polymer can be a halogenated polymer (e.g., a fluorinated polymer).

The first polymer can have a backbone and side groups that are more polar than the backbone.

The first polymer can have a molecular weight of from about 500 to about 15,000.

The first polymer can be substantially linear.

The particle can include a second polymer.

The particle can include a polysaccharide (e.g., alginate).

The particle can be substantially spherical.

The particle can have a coating over its surface region. The coating can be bioabsorbable. The coating can be a polymer. The coating can be a polysaccharide, a polysaccharide derivative, or an inorganic ionic salt. The coating can include a therapeutic agent.

The interior region of the particle can have a density of large pores and the surface region of the particle can have a density of large pores. The density of large pores of the interior region can be greater than the density of large pores at the surface region.

The particle can include a therapeutic agent. The therapeutic agent can be bound to the first polymer. The therapeutic agent can be disposed within the pores of the interior region.

The particle can include a ferromagnetic material, a material that is visible by magnetic resonance imaging (an MRI-visible material), and/or a radiopaque material.

The carrier fluid can be a saline solution.

The carrier fluid can be a contrast agent.

The carrier fluid can include a surfactant. For example, the carrier fluid can include from about 0.05 percent by weight to about one percent by weight (e.g., about 0.1 percent by weight, about 0.5 percent by weight) of the surfactant.

The gelling compound can be a polysaccharide (e.g., alginate).

The mixture can include a second polymer.

The second polymer can be a polyvinyl alcohol, a polyacrylic acid, a polymethacrylic acid, a poly vinyl sulfonate, a carboxymethyl cellulose, a hydroxyethyl cellulose, a substituted cellulose, a polyacrylamide, a polyethylene glycol, a polyamide, a polyurea, a polyurethane, a polyester, a polyether, a polystyrene, a polysaccharide, a polylactic acid, a polyethylene, a polymethylmethacrylate, a polycaprolactone, a polyglycolic acid, a poly(lactic-co-glycolic) acid, or a combination thereof.

The method can include forming drops of the mixture, contacting the drops with a gelling agent, reacting the second polymer, and/or removing the gelling compound.

The method can include combining the particles with a pharmaceutically acceptable medium.

The method can include bonding a therapeutic agent to the first polymer.

The method of administration can be by percutaneous injection.

The method of administration can be by a catheter.

The method can include releasing a therapeutic agent from the first polymer.

Embodiments can include one or more of the following advantages.

In some embodiments, a particle with a surface preferential material can be tailored or designed to release a therapeutic agent at a desired time and/or location. For example, such a particle can be used to deliver a therapeutic agent in a relatively rapid manner and/or to a targeted site (e.g., during an embolization procedure).

In certain embodiments, a sustained, controlled-dosage release of an agent (e.g., a therapeutic agent) can be effected by an agent-containing particle that includes a surface preferential material (e.g., to which the agent is bound).

In some embodiments, a burst release of an agent (e.g., a therapeutic agent) can be effected by an agent-containing particle that includes a surface preferential material by, for example, loading the surface preferential material with agent.

In certain embodiments, a combination sustained, controlled-dosage release and burst release of agent (e.g., therapeutic agent) can be obtained with an agent-containing particle that includes a surface preferential material by, for example, coating the surface of the particle with agent and loading the surface preferential material and/or the interior region of the particle with agent. In certain embodiments, the agent that is coated on the surface can first be released in a controlled manner, followed by a burst release of the agent that is loaded in the surface preferential material and/or in the interior region of the particle.

In embodiments, loading the agent onto and/or into the surface preferential material of the particle can target (e.g., physically target) the agent to a desired site (e.g., a site having a condition to be treated, such as a site having a cancer condition). This can allow for a more efficient use of agent. For example, targeted delivery can permit a lower dosage of agent to be used (e.g., thereby reducing side effects due to the agent).

Features and advantages are in the description, drawings, and claims.

DESCRIPTION OF DRAWINGS

FIG. 3A is a schematic illustrating an embodiment of injection of an embolic composition including embolic particles into a vessel.

DETAILED DESCRIPTION

Figure 1:
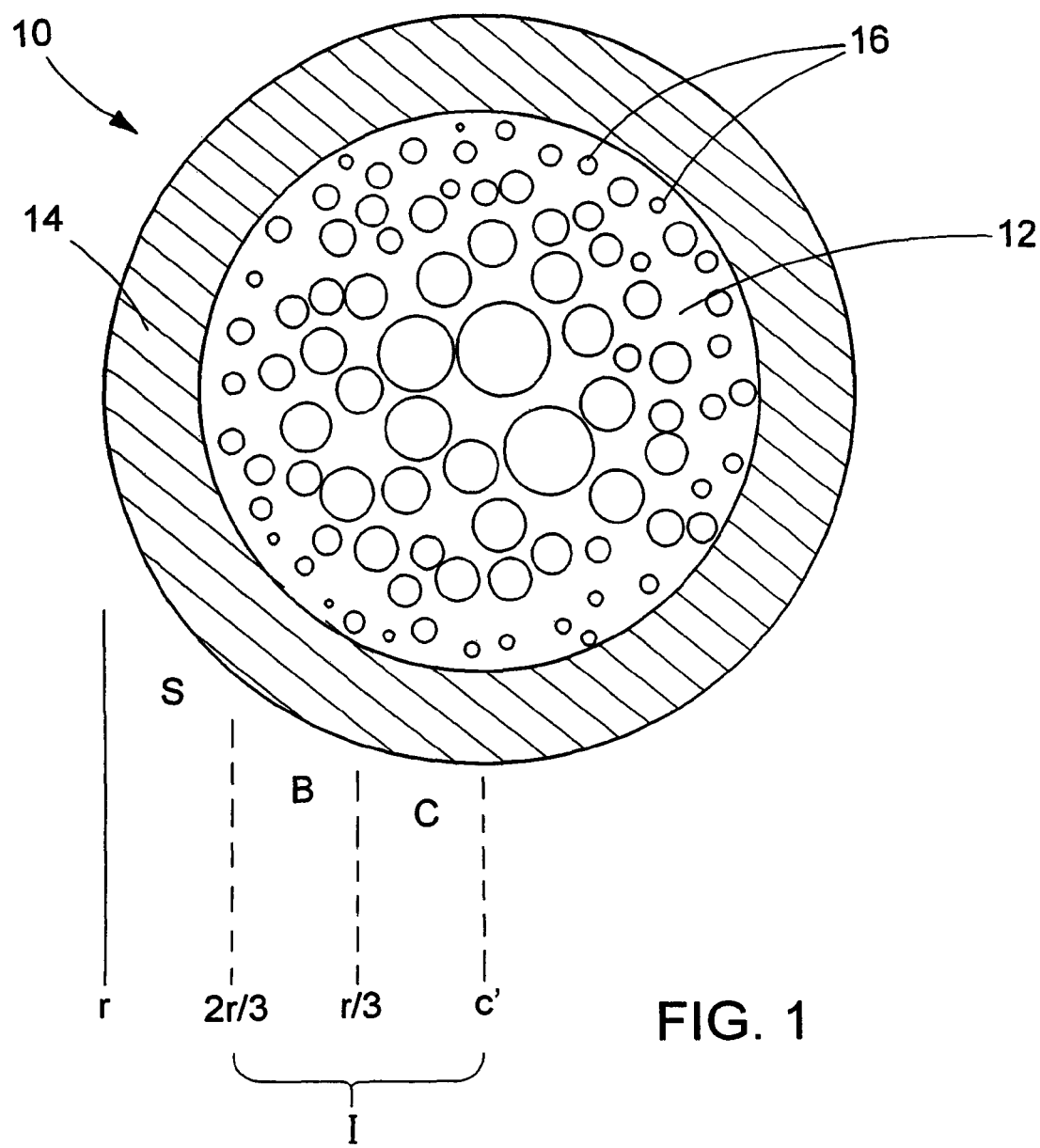
FIG. 1 is a cross-sectional view of an embodiment of a particle.

FIG. 1 shows a substantially spherical particle 10 that includes a matrix material 12 (e.g., a polyvinyl alcohol), a surface preferential material 14 (e.g., a fluorinated polymer), and pores 16. Surface preferential material 14 has one or more therapeutic agents (e.g., drugs) bonded thereto.

Particle 10 can be considered to include a center region, C, from the center c' of particle 10 to a radius of about r/3, a body region, B, from about r/3 to about 2 r/3, and a surface region, S, from about 2r/3 to r. Particle 10 can also be considered to include an interior region, I, from the center c' of particle 10 to a radius of about 2r/3. Region I represents the sum of regions B and C.

In general, the amount of surface preferential material 14 at region S is greater than the amount of surface preferential material 14 in region I. In some embodiments, region I is substantially devoid of surface preferential material 14.

The difference between the weight percent of surface preferential material 14 at region S and the weight percent of surface preferential material 14 in region I can be at least about 30 weight percent (e.g., at least about 35 weight percent, at least about 40 weight percent, at least about 45 weight percent, at least about 50 weight percent, at least about 55 weight percent, at least about 60 weight percent, at least about 65 weight percent, at least about 70 weight percent, at least about 75 weight percent, at least about 80 weight percent, at least about 85 weight percent, at least about 90 weight percent, at least about 95 weight percent), and/or at most about 100 weight percent (e.g., at most about 95 weight percent, at most about 90 weight percent, at most about 85 weight percent, at most about 80 weight percent, at most about 75 weight percent, at most about 70 weight percent, at most about 65 weight percent, at most about 60 weight percent, at most about 55 weight percent, at most about 50 weight percent, at most about 45 weight percent, at most about 40 weight percent, at most about 35 weight percent).

In general, region S can include from about 0.1 weight percent to about 100 weight percent (e.g., from about 20 weight percent to about 100 weight percent, from about 25 weight percent to about 75 weight percent, from about 30 weight percent to about 75 weight percent) of surface preferential material 14. In some embodiments, region S can include at least about 0.1 weight percent (e.g., at least about 0.2 weight percent, at least about 0.5 weight percent, at least about 0.7 weight percent, at least about one weight percent, at least about five weight percent, at least about ten weight percent, at least about 15 weight percent, at least about 20 weight percent, at least about 25 weight percent, at least about 30 weight percent, at least about 35 weight percent, at least about 40 weight percent, at least about 45 weight percent, at least about 50 weight percent, at least about 55 weight percent, at least about 60 weight percent, at least about 65 weight percent, at least about 70 weight percent, at least about 75 weight percent, at least about 80 weight percent, at least about 85 weight percent, at least about 90 weight percent, at least about 95 weight percent, at least about 99 weight percent), and/or at most about 100 weight percent (e.g., at most about 99 weight percent, at most about 95 weight percent, at most about 90 weight percent, at most about 85 weight percent, at most about 80 weight percent, at most about 75 weight percent, at most about 70 weight percent, at most about 65 weight percent, at most about 60 weight percent, at most about 55 weight percent, at most about 50 weight percent, at most about 45 weight percent, at most about 40 weight percent, at most about 35 weight percent, at most about 30 weight percent, at most about 25 weight percent, at most about 20 weight percent, at most about 15 weight percent, at most about ten weight percent, at most about five weight percent, at most about one weight percent, at most about 0.7 weight percent, at most about 0.5 weight percent, at most about 0.2 weight percent), of surface preferential material 14.

Region I generally can include a lower weight percent of surface preferential material 14 than region S. For example, region I can include from about 0.1 weight percent to about 50 weight percent of surface preferential material 14. In some embodiments, region I can include at most about 50 weight percent (e.g., at most about 45 weight percent, at most about 40 weight percent, at most about 35 weight percent, at most about 30 weight percent, at most about 25 weight percent, at most about 20 weight percent, at most about 15 weight percent, at most about ten weight percent, at most about five weight percent, at most about three weight percent, at most about two weight percent, at most about one weight percent, at most about 0.5 weight percent, at most about 0.2 weight percent), and/or at least about 0.1 weight percent (e.g., at least about 0.2 weight percent, at least about 0.5 weight percent, at least about one weight percent, at least about two weight percent, at least about three weight percent, at least about five weight percent, at least about ten weight percent, at least about 15 weight percent, at least about 20 weight percent, at least about 25 weight percent, at least about 30 weight percent, at least about 35 weight percent, at least about 40 weight percent, at least about 45 weight percent), of surface preferential material 14. In some embodiments, region I can be substantially devoid of surface preferential material 14. In certain embodiments, region I may not include any surface preferential material 14.

In general, the amount of surface preferential material 14 in particle 10 can be varied as desired. In some embodiments, particle 10 can include at least about 0.1 weight percent (e.g., at least about 0.2 weight percent, at least about 0.5 weight percent, at least about one weight percent, at least about five weight percent, at least about ten weight percent, at least about 15 weight percent, at least about 20 weight percent, at least about 25 weight percent, at least about 30 weight percent, at least about 35 weight percent, at least about 40 weight percent, at least about 45 weight percent, at least about 50 weight percent, at least about 55 weight percent, at least about 60 weight percent, at least about 65 weight percent, at least about 70 weight percent, at least about 75 weight percent, at least about 80 weight percent, at least about 85 weight percent), and/or at most about 90 weight percent (e.g., at most about 85 weight percent, at most about 80 weight percent, at most about 75 weight percent, at most about 70 weight percent, at most about 65 weight percent, at most about 60 weight percent, at most about 55 weight percent, at most about 50 weight percent, at most about 45 weight percent, at most about 40 weight percent, at most about 35 weight percent, at most about 30 weight percent, at most about 25 weight percent, at most about 20 weight percent, at most about 15 weight percent, at most about ten weight percent, at most about five weight percent, at most about one weight percent, at most about 0.5 weight percent, at most about 0.2 weight percent), of surface preferential material 14. In certain embodiments, particle 10 can include from about 0.1 weight percent to about 90 weight percent (e.g., from about 0.1 weight percent to about 80 weight percent, from about ten weight percent to about 80 weight percent, from about 25 weight percent to about 85 weight percent, from about 0.1 weight percent to about 60 weight percent, from about 0.25 weight percent to about 50 weight percent, from about five weight percent to about 50 weight percent, from about 15 weight percent to about 35 weight percent, from about 0.25 weight percent to about 20 weight percent, from about 0.25 weight percent to about ten weight percent, from about one weight percent to about ten weight percent) of surface preferential material 14. In some embodiments (e.g., when particle 10 includes from about 0.25 weight percent to about 20 weight percent of surface preferential material 14), region S can include from about 25 weight percent to about 70 weight percent of surface preferential material 14. In certain embodiments (e.g., when particle 10 includes from about one weight percent to about ten weight percent of surface preferential material 14), region S can include from about 30 weight percent to about 50 weight percent of surface preferential material 14.

In general, the amount of matrix material 12 in region S is substantially less than the amount of matrix material 12 in region I.

Generally, region I can include from about 30 weight percent to about 100 weight percent of matrix material 12. In some embodiments, region I can include at least about 30 weight percent (e.g., at least about 35 weight percent, at least about 40 weight percent, at least about 45 weight percent, at least about 50 weight percent, at least about 55 weight percent, at least about 60 weight percent, at least about 65 weight percent, at least about 70 weight percent, at least about 75 weight percent, at least about 80 weight percent, at least about 85 weight percent, at least about 90 weight percent, at least about 95 weight percent), and/or at most about 100 weight percent (e.g., at most about 95 weight percent, at most about 90 weight percent, at most about 85 weight percent, at most about 80 weight percent, at most about 75 weight percent, at most about 70 weight percent, at most about 65 weight percent, at most about 60 weight percent, at most about 55 weight percent, at most about 50 weight percent, at most about 45 weight percent, at most about 40 weight percent, at most about 35 weight percent), of matrix material 12. In some embodiments (e.g., when particle 10 includes from about ten weight percent to about 97 weight percent of matrix material 12, when particle 10 includes from about ten weight percent to about 90 weight percent of matrix material 12), region I can include from about 30 weight percent to about 100 weight percent of matrix material 12. In certain embodiments (e.g., when particle 10 includes from about ten weight percent to about 90 weight percent of matrix material 12, when particle 10 includes from about 40 weight percent to about 97 weight percent of matrix material 12), region I can include from about 60 weight percent to about 100 weight percent of matrix material 12.

In some embodiments, region S can include matrix material 12, in addition to including surface preferential material 14. For example, region S can include from about 0.1 weight percent to about 75 weight percent (e.g., from about 0.1 weight percent to about 50 weight percent) of matrix material 12. In certain embodiments, region S can include at most about 75 weight percent (e.g., at most about 70 weight percent, at most about 65 weight percent, at most about 60 weight percent, at most about 55 weight percent, at most about 50 weight percent, at most about 45 weight percent, at most about 40 weight percent, at most about 35 weight percent, at most about 30 weight percent, at most about 25 weight percent, at most about 20 weight percent, at most about 15 weight percent, at most about ten weight percent, at most about five weight percent, at most about one weight percent, at most about 0.5 weight percent, at most about 0.2 weight percent), and/or at least about 0.1 weight percent (e.g., at least about 0.2 weight percent, at least about 0.5 weight percent, at least about one weight percent, at least about five weight percent, at least about ten weight percent, at least about 15 weight percent, at least about 20 weight percent, at least about 25 weight percent, at least about 30 weight percent, at least about 35 weight percent, at least about 40 weight percent, at least about 45 weight percent, at least about 50 weight percent, at least about 55 weight percent, at least about 60 weight percent, at least about 65 weight percent, at least about 70 weight percent), of matrix material 12. In some embodiments, region S can be substantially devoid of matrix material 12. In certain embodiments, region S may not include any matrix material 12.

In general, the amount of matrix material 12 in particle 10 can be varied as desired. Particle 10 can include from about ten weight percent to about 100 weight percent (e.g., from about 40 weight percent to about 100 weight percent) of matrix material 12. In some embodiments, particle 10 can include at most about 100 weight percent (e.g., at most about 99 weight percent, at most about 97 weight percent, at most about 95 weight percent, at most about 90 weight percent, at most about 80 weight percent, at most about 70 weight percent, at most about 60 weight percent, at most about 50 weight percent, at most about 40 weight percent, at most about 30 weight percent, at most about 20 weight percent), and/or at least about ten weight percent (e.g., at least about 20 weight percent, at least about 30 weight percent, at least about 40 weight percent, at least about 50 weight percent, at least about 60 weight percent, at least about 70 weight percent, at least about 80 weight percent, at least about 90 weight percent, at least about 95 weight percent, at least about 97 weight percent, at least about 99 weight percent), of matrix material 12.

Matrix material 12 can be formed of one or more polymers (e.g., biocompatible polymers). Examples of polymers include polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polyolefins, polypropylenes, polymethylmethacrylates, polycaprolactones, polyglycolic acids, poly(lactic-co-glycolic) acids (e.g., poly(d-lactic-co-glycolic) acids), polysulfones, polyethersulfones, polycarbonates, nylons, silicones, linear or crosslinked polysilicones, and copolymers or mixtures thereof. In some embodiments, matrix material 12 can be substantially formed of a highly water insoluble, high molecular weight polymer. An example of such a polymer is a high molecular weight polyvinyl alcohol (PVA) that has been acetalized. Matrix material 12 can be substantially pure intrachain 1,3-acetalized PVA and substantially free of animal derived residue such as collagen. In some embodiments, particle 10 includes a minor amount (e.g., about 2.5 weight percent or less, about one weight percent or less, about 0.2 weight percent or less) of a gelling material (e.g., a polysaccharide, such as alginate). In certain embodiments, the majority (e.g., at least about 75 weight percent, at least about 90 weight percent, at least about 95 weight percent) of matrix material 12 is a bioabsorbable polymer (e.g., polysaccharide, such as alginate). Matrix material 12 can include, for example, polyvinyl alcohol, alginate, or both polyvinyl alcohol and alginate.

In some embodiments, the type of matrix material 12 used in particle 10 affects the weight percent of surface preferential material 14 at region S of particle 10. For example, if matrix material 12 is a polystyrene, a silicone, a polyurethane, a polypropylene, a polysulfone, or a nylon, then the weight percent of surface preferential material 14 at region S of particle 10 can be relatively high (e.g., 80 weight percent). The weight percent of surface preferential material 14 at region S can be relatively high in such embodiments because, for example, surface preferential material 14 may migrate relatively easily to region S when added to particle 10 during or after the formation of particle 10. However, in some embodiments, if matrix material 12 is, for example, a polymer that is loaded with a radiopaque material, then the weight percent of the same surface preferential material 14 at region S of particle 10 can be relatively low (e.g., 30 weight percent). The weight percent of surface preferential material 14 at region S can be relatively low in such embodiments because, for example, the surface preferential material may be more restricted in its migration toward region S when added to particle 10 during or after the formation of particle 10. Properties of matrix material 12 that can affect the degree of migration of surface preferential material 14 to region S of particle 10 can include density and/or viscosity.

The characteristics of a particle (such as the amount and/or type of materials present at the particle surface) that includes matrix material 12 and surface preferential material 14 can be determined using, for example, one or more of the analytical services (e.g., Proton NMR) provided by Jordi FLP (Bellingham, Mass.).

Surface preferential material 14 can be, for example, a polymer (e.g., a biocompatible polymer). In some embodiments, the polymer can have the following general formula:

$$D\text{-}B\text{-}[O\text{-}(A\text{-}O)_n\text{-}B]_m\text{-}D \qquad (1)$$

In formula (1), $[O\text{-}(A\text{-}O)_n\text{-}B]_m$ is a central portion, O is a first oligomeric segment, A is a second coupling segment that links one O to another O within the central portion, D is a polyfluoro oligomeric group, and B is a first coupling segment that links the central portion to D. Generally, n is from zero to 20 (e.g., from two to ten), and m is from one to 20 (e.g., from one to ten). A therapeutic agent can be bound to one or both of the B components of the above surface preferential material.

In general, first oligomeric segment O is a relatively short length of a repeating unit or units. For example, O can have less than about 20 monomeric units and a molecular weight of less than 5000. In some embodiments, O can be a polyurethane, a polyurea, a polyamide, a polyalkylene oxide, a polycarbonate, a polyester, a polylactone, a polysilicone, a polyethersulfone, a polyolefin, a polyvinyl, a polypeptide polysaccharide, or an ether and amine linked segment thereof.

Second coupling segment A is a molecule that is capable of covalently coupling 0 units together and of forming the second coupling segments within the central portion. Typically, A can have a molecular weight ranging from 40 to 700 and can have difunctionality to permit coupling of two O units. In some embodiments, A can be a diamine, a diisocyanate, a disulfonic acid, a dicarboxylic acid, a diacid chloride, or a dialdehyde. Terminal hydroxyls, amines or carboxylic acids on the O molecules can react with diamines to form O-amides; can react with diisocyanates to form O-urethanes, O-ureas, O-amides; can react with disulfonic acids to form O-sulfonates, O-sulfonamides; can react with dicarboxylic acids to form O-esters, O-amides; can react with diacid chlorides to form O-esters, O-amides; and can react with dialdehydes to form O-acetal, O-imines.

First coupling segment B is a molecule that can provide primary functional groups capable of covalently coupling with the O/A central portion and D components. Additionally, B has secondary functional chemistry for coupling, e.g., therapeutic agents, such as drugs or bioactive components. Typically, B can have a molecular weight ranging from about 40 to about 700. In some embodiments, B can be a functionalized diamine, a functionalized diisocyanate, a functionalized disulfonic acid, a functionalized dicarboxylic acid, a functionalized diacid chloride or a functionalized dialdehyde, in which the functionalized component has secondary functional chemistry that is accessed for chemical attachment of, for example, therapeutic agents. Such secondary groups can be, for example, esters, carboxylic acid salts, sulfonic acid salts, phosphonic acid salts, thiols, vinyls, or secondary amines. Again, terminal hydroxyls, amines or carboxylic acids on the O/A intermediates can react with diamines to form O-amides; can react with diisocyanates to form O-urethanes, O-ureas, O-amides; can react with disulfonic acids to form O-sulfonates, O-sulfonamides; can react with dicarboxylic acids to form O-esters, O-amides; can react with diacid chlorides to form O-esters, O-amides; and can react with dialdehydes to form O-acetal, O-imines.

In some embodiments, D can be a radical of the general formula $CF_3(CF_2)_pCH_2CH_2-$ in which p is from two to 20. In certain embodiments, D can have the general formula $CF_3(CF_2)_m(CH_2CH_{20})_q-$ in which q is from one to ten and m is from one to 20. In certain embodiments, D is the perfluoroalkyl group $C_8F_{17}CH_2CH_2-$.

Without wishing to be bound by theory, it is believed that a surface preferential material that has formula (1) tends to migrate to the surface of matrix material 12 when added to matrix material 12. In some embodiments, it is believed that the oligomeric fluorine tails of such a surface preferential material can (e.g., when they are immiscible with matrix material 12) help to carry the surface preferential material to the surface of matrix material 12. If a therapeutic agent is bound to the surface preferential material (e.g., to the B components of the surface preferential material), then the therapeutic agent can migrate to the surface of matrix material 12 along with the surface preferential material.

Further examples of surface preferential materials 14 are polymers that include lysine diisocyanate, a fraction of BA-L™ (a fluoroalcohol available from DuPont), and one of the following: polycarbonate diol; polyethylene tetramethylene oxide; polydimethylsiloxane-bis(3-aminopropyl) terminated; trimethyl-1,6-diisocyanatohexane/dihydroxy diphenylsulfone; polyethylene-butylene copolymer diol; 1,6-hexamethylene diisocyanate/polyethylene tetramethylene oxide/polypropylene oxide diol; or amine-terminated oligophenylalanine Another example of surface preferential material 14 is a polymer that includes segmented polyurethane/DABs, polyethylene tetramethylene oxide, and a fraction of BA-L™.

In some embodiments, surface preferential material 14 is a polymer that includes segmented polyurethane/DABs, polyethylene tetramethylene oxide, and a fraction of BA-L™.

Although surface preferential material 14 has been described as being a polymer, in some embodiments, surface preferential material 14 is a non-polymeric material.

In certain embodiments, surface preferential material 14 can be a material that makes particle 10 relatively lubricious and thereby improves the deliverability of particle 10 (e.g., by decreasing the friction between particle 10 and a device used to deliver particle 10).

In certain embodiments, surface preferential material 14 can be bioerodible, such that surface preferential material 14 can eventually break down in the body and either be dispersed throughout the body or excreted from the body.

Surface preferential material 14 can have a molecular weight that is at least about 500 (e.g., at least about 1,000; at least about 2,000; at least about 3,000; at least about 4,000; at least about 5,000; at least about 6,000; at least about 7,000; at least about 8,000; at least about 9,000; at least about 10,000; at least about 11,000; at least about 12,000; at least about 13,000; at least about 14,000), and/or at most about 15,000 (e.g., at most about 14,000; at most about 13,000; at most about 12,000; at most about 11,000; at most about 10,000; at most about 9,000; at most about 8,000; at most about 7,000; at most about 6,000; at most about 5,000; at most about 4,000; at most about 3,000; at most about 2,000; at most about 1,000). The molecular weight of a polymer can be measured by, for example, gel permeation chromatography.

Surface preferential materials are described, for example, in Santerre, U.S. Published Patent Application No. US 2003/0097120 A1, which is incorporated herein by reference.

As noted above, surface preferential material 14 of particle 10 is bound to one or more therapeutic agents (e.g., drugs). Surface preferential material 14 can be selected or designed to release the therapeutic agent over a period of time, and/or to release the agent when triggered by certain factors (e.g., exposure to the bloodstream, temperature, pH, light).

Therapeutic agents include agents that are negatively charged, positively charged, amphoteric, or neutral. Therapeutic agents can be, for example, materials that are biologically active to treat physiological conditions; pharmaceutically active compounds; gene therapies; nucleic acids with and without carrier vectors; oligonucleotides; gene/vector systems; DNA chimeras; compacting agents (e.g., DNA compacting agents); viruses; polymers; hyaluronic acid; proteins (e.g., enzymes such as ribozymes); cells (of human origin, from an animal source, or genetically engineered); stem cells; immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); anti-inflammatory agents; calcium entry blockers; antineoplastic/antiproliferative/anti-mitotic agents (e.g., paclitaxel, doxorubicin, cisplatin); antimicrobials; anesthetic agents; anti-coagulants; vascular cell growth promoters; vascular cell growth inhibitors; cholesterol-lowering agents; vasodilating agents; agents which interfere with endogenous vasoactive mechanisms; and survival genes which protect against cell death. Therapeutic agents are described, for example, in co-pending U.S. patent application Ser. No. 10/615,276, filed on Jul. 8, 2003, and entitled "Agent Delivery Particle", which is incorporated herein by reference.

In some embodiments, other regions of particle 10 can include a therapeutic agent. For example, region I of particle 10 can include a therapeutic agent. In certain embodiments, pores 16 of particle 10 can include a therapeutic agent.

In general, particle 10 can have a diameter of from about ten microns to about 3,000 microns. In some embodiments, particle 10 can have a diameter of about 3,000 microns or less (e.g., about 2,500 microns or less; about 2,000 microns or less; about 1,500 microns or less; about 1,200 microns or less; about 1,000 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,000 microns or more; about 1,200 microns or more; about 1,500 microns or more; about 2,000 microns or more; about 2,500 microns or more).

In certain embodiments, the diameter of particle 10 can be from about 100 microns to about 700 microns; from about 500 microns to about 700 microns; from about 100 microns to about 500 microns; from about 100 microns to about 300 microns; from about 300 microns to about 500 microns; from about 500 microns to about 1,200 microns; from about 500 microns to about 700 microns; from about 700 microns to about 900 microns; from about 900 microns to about 1,200 microns.

Regions C, B, and S can be characterized by the relative size of pores 16 present in particle 10 in each region, the density of pores 16 (the number of pores 16 per unit volume of particle 10) in each region, and/or the mass density (the density of matrix material 12 and surface preferential material 14 mass per unit volume of particle 10) in each region.

In general, the mean size of pores 16 in region C of particle 10 is greater than the mean size of pores 16 at region S of particle 10. In some embodiments, the mean size of pores 16 in region C of particle 10 is greater than the mean size of pores 16 in region B particle 10, and/or the mean size of pores 16 in region B of particle 10 is greater than the mean size of pores 16 at region S particle 10. In some embodiments, the mean size of pores 16 in region C is about 20 microns or more (e.g., about 30 microns or more, from about 20 microns to about 35 microns). In certain embodiments, the mean size of pores 16 in region B is about 18 microns or less (e.g. about 15 microns or less, from about 18 microns to about two microns). In some embodiments, the mean size of pores 16 at region S is about one micron or less (e.g. from about 0.1 micron to about 0.01 micron). In certain embodiments, the mean size of pores 16 in region B is from about 50 percent to about 70 percent of the mean size of pores 16 in region C, and/or the mean size of pores 16 at region S is about ten percent or less (e.g., about two percent or less) of the mean size of pores 16 in region B. In some embodiments, the surface of particle 10 and/or its region S is/are substantially free of pores having a diameter greater than about one micron (e.g., greater than about ten microns). In certain embodiments, the mean size of pores 16 in the region from 0.8r to r (e.g., from 0.9r to r) is about one micron or less (e.g., about 0.5 micron or less, about 0.1 micron or less). In some embodiments, pores 16 in the region from the center of particle 10 to 0.9r (e.g., from the center of particle 10 to 0.8r) are about ten microns or greater and/or have a mean size of from about two microns to about 35 microns. In certain embodiments, the mean size of pores 16 in the region from 0.8r to r (e.g., from 0.9r to r) is about five percent or less (e.g., about one percent or less, about 0.3 percent or less) of the mean size of pores 16 in the region from the center to 0.9r. In some embodiments, the largest pores in particle 10 can have a size in the range of about one percent or more (e.g., about five percent or more, about ten percent or more) of the diameter of particle 10. The size of pores 16 in particle 10 can be measured by viewing a cross-section of particle 10. For irregularly shaped (nonspherical) pores, the maximum visible cross-section is used.

Generally, the density of pores 16 in region C of particle 10 is greater than the density of pores 16 at region S of particle 10. In some embodiments, the density of pores 16 in region C of particle 10 is greater than the density of pores 16 in region B of particle 10, and/or the density of pores 16 in region B of particle 10 is greater than the density of pores 16 at region S of particle 10.

In general, the mass density in region C of particle 10 is less than the mass density at region S of particle 10. In some embodiments, the mass density in region C of particle 10 is less than the mass density in region B of particle 10, and/or the mass density in region B of particle 10 is less than the mass density at region S of particle 10.

In general, the density of particle 10 (e.g., as measured in grams of material per unit volume) is such that it can be readily suspended in a carrier fluid (e.g., a pharmaceutically acceptable carrier, such as a saline solution, a contrast solution, or a mixture thereof) and remain suspended during delivery. In some embodiments, the density of particle 10 is from about 1.1 grams per cubic centimeter to about 1.4 grams per cubic centimeter. As an example, for suspension in a saline-contrast solution, the density of particle 10 can be from about 1.2 grams per cubic centimeter to about 1.3 grams per cubic centimeter.

In certain embodiments the region of small pores near the surface of particle 10 can be relatively stiff and incompressible, which can enhance resistance to shear forces and abrasion. In addition, the variable pore size profile can produce a symmetric compressibility and, it is believed, a compressibility profile. As a result, particle 10 can be relatively easily compressed from a maximum, at rest diameter to a smaller, compressed first diameter. Compression to an even smaller diameter, however, may involve substantially greater force. Without wishing to be bound by theory, it is believed that a variable compressibility profile can be the result of a relatively weak, collapsible inter-pore wall structure in the center region of particle 10 (where the pores are relatively large), and a stiffer inter-pore wall structure near the surface of particle 10 (where the pores are more numerous and relatively small). It is further believed that a variable pore size profile can enhance elastic recovery after compression. It is also believed that the pore structure can influence the density of particle 10 and the rate of carrier fluid or body fluid uptake.

In some embodiments, a plurality of the particles (e.g., in an embolic composition) can be delivered through a catheter having a lumen with a cross-sectional area that is smaller (e.g., about 50 percent or less) than the uncompressed cross-sectional area of the particles. In such embodiments, the particles are compressed to pass through the catheter for delivery into the body. Typically, the compression force is provided indirectly, by depressing the syringe plunger to increase the pressure applied to the carrier fluid. In general, the particles are relatively easily compressed to diameters sufficient for delivery through the catheter into the body. The relatively robust, rigid surface region of the particles can resist abrasion when the particles contact hard surfaces such as syringe surfaces, hard plastic or metal stopcock surfaces, and/or the catheter lumen wall (made of, e.g., Teflon) during delivery. Once in the body, the particles can substantially recover to original diameter and shape for efficient transport in the carrier and body fluid stream. At the point of occlusion, the particles can again compress as they aggregate in the occlusion region. The particles can form a relatively dense occluding mass. The compression of the particles in the body is generally determined by the force provided by body fluid flow in the lumen. In some embodiments, the compression may be limited by the compression profile of the particles, and the number of particles needed to occlude a given diameter may be reduced.

In certain embodiments, the sphericity of particle 10 after compression in a catheter (e.g., after compression to about 50 percent or more of the cross-sectional area of particle 10) is about 0.8 or more (e.g., about 0.85 or more, about 0.9 or more, about 0.95 or more, about 0.97 or more). Particle 10 can be, for example, manually compressed, essentially flattened, while wet to about 50 percent or less of its original diameter and then, upon exposure to fluid, regain a sphericity of about 0.8 or more (e.g., about 0.85 or more, about 0.9 or more, about 0.95 or more, about 0.97 or more). The sphericity of a particle can be determined using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures particles in an image in the form of a fiber, rod or sphere. The sphericity of a particle, which is computed as Da/Dp (where Da=$\sqrt{(4A/\pi)}$; Dp=P/$\pi$; A=pixel area; P=pixel perimeter), is a value from zero to one, with one representing a perfect circle.

Porous particles are described, for example, in U.S. patent application Ser. No. 10/637,130, filed on Aug. 8, 2003, and entitled "Embolization", which is incorporated herein by reference.

In general, various methods can be used to prepare particle 10. In some embodiments, particle 10 is formed using a drop generator.

Figure 2A:
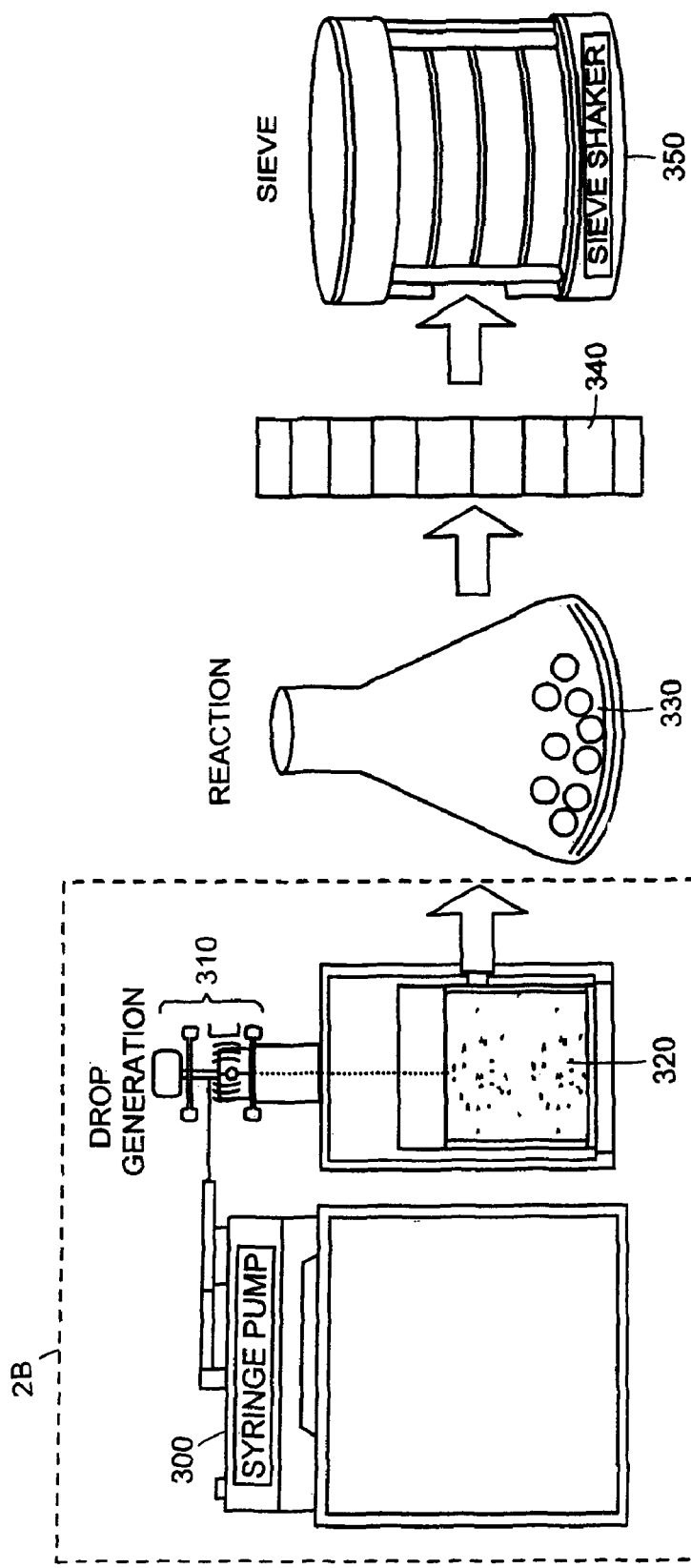
FIG. 2A is a schematic of an embodiment of a system for manufacturing particles.
Figure 2B:
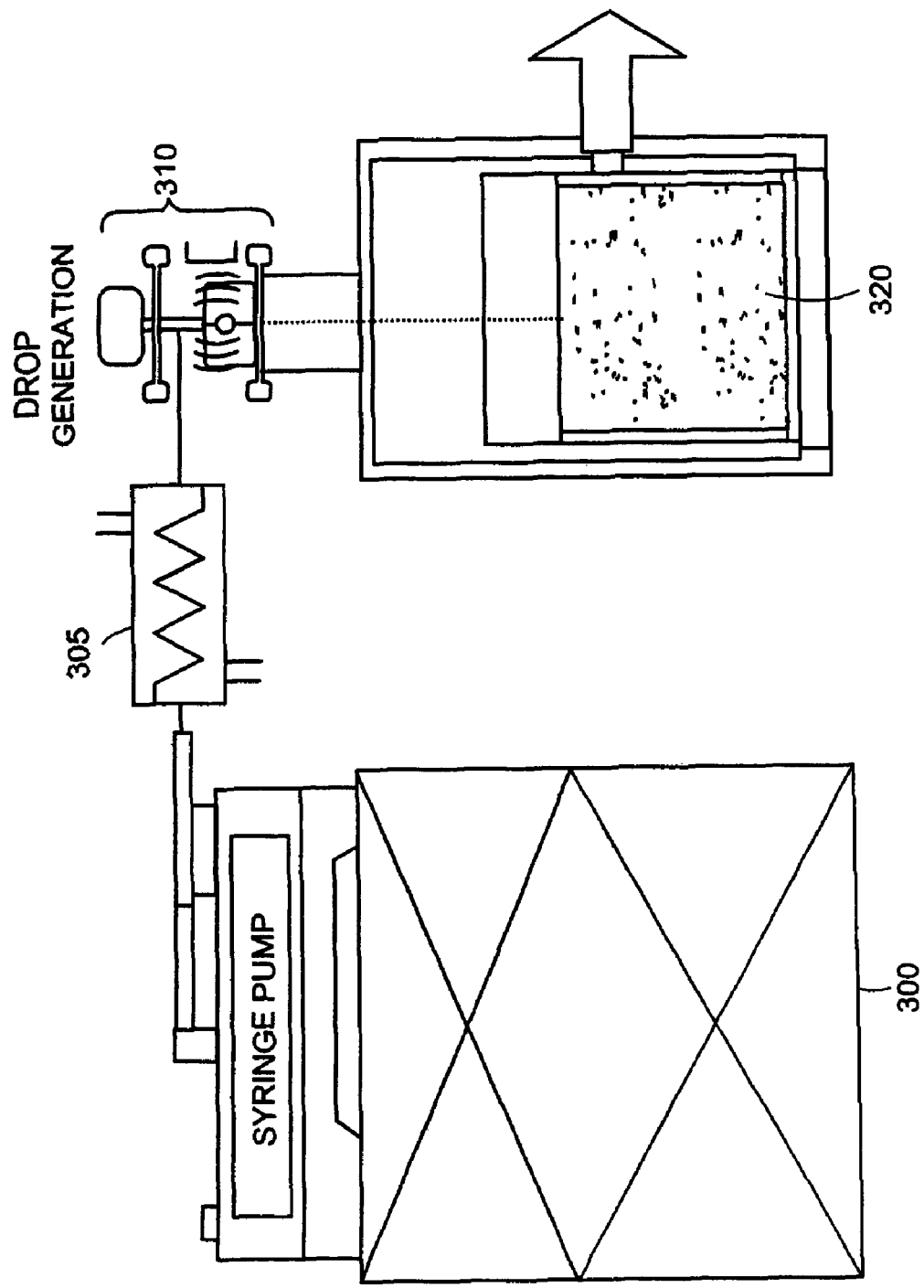
FIG. 2B is an enlarged schematic of region 2B in FIG. 2A.

FIG. 2A shows an embodiment of a system for producing particle 10. The system includes a flow controller 300, a drop generator 310, a gelling vessel 320, a reactor vessel 330, a gel dissolution chamber 340 and a filter 350. As shown in FIG. 2B, flow controller 300 delivers a solution that contains matrix material 12 (e.g., one or more polymers) and a gelling precursor (e.g., alginate) to a viscosity controller 305, which heats the solution to reduce viscosity prior to delivery to drop generator 310. The solution passes through an orifice in a nozzle in drop generator 310, forming drops of the solution. The drops are then directed into gelling vessel 320, where the drops contact a gelling agent (e.g., calcium chloride) that converts the gelling precursor from a solution form into a gel form, stabilizing the drops. The gel-stabilized drops are transferred from gelling vessel 320 to reactor vessel 330, where the polymer in the gel-stabilized drops is reacted (e.g., cross-linked), forming precursor particles. The precursor particles are transferred to gel dissolution chamber 340, where the gelling precursor (which was converted to a gel) is removed. The particles are then filtered in filter 350 to remove debris, and are sterilized and packaged as an embolic composition including the particles. Methods of making particles are described, for example, in U.S. patent application Ser. No. 10/637,130, filed on Aug. 8, 2003, and entitled "Embolization", which is incorporated herein by reference.

In some embodiments in which a drop generator is used in the preparation of particle 10, surface preferential material 14 is included in the solution delivered by the drop generator, and the solution is processed as described above to form particle 10. In certain embodiments in which a drop generator is used in the preparation of particle 10, surface preferential material 14 is included in the gelling vessel so that surface preferential material 14 is incorporated into the drop when the drop contacts the gelling agent. Combinations of these methods can be used.

In some embodiments, surface preferential material 14 is added to particle 10 in a separate operation. For example, surface preferential material 14 can be applied to the surface of particle 10 by compounding surface preferential material 14 with one or more of the coating materials (described below) and then applying the compounded coating material to the surface of particle 10. In certain embodiments, surface preferential material 14 can be placed in particle 10 (e.g., in one or more pores 16 or cavities of particle 10). In embodiments in which surface preferential material 14 is in liquid form prior to being incorporated into particle 10, surface preferential material 14 can be incorporated into particle 10 by, for example, absorption. Combinations of these methods can be used. For example, in some embodiments, one surface preferential material can be incorporated into a cavity in a particle, while another surface preferential material (either the same as, or different from, the first surface preferential material) can be absorbed through the surface of the particle.

In general, when surface preferential material 14 is added to particle 10 (e.g., during preparation of particle 10 or in a separate operation), surface preferential material 14 migrates toward region S of particle 10, thus typically causing region S to include a greater weight percent of surface preferential material 14 than region I.

In some embodiments, multiple particles are combined with a carrier fluid (e.g., a saline solution, a contrast agent, or both) to form an embolic composition. Such embolic compositions can be delivered to various sites in the body, including, for example, sites having cancerous lesions, such as the breast, prostate, lung, thyroid, or ovaries. The embolic compositions can be used in, for example, neural, pulmonary, and/or AAA (abdominal aortic aneurysm) applications. The compositions can be used in the treatment of, for example, fibroids, tumors, internal bleeding, arteriovenous malformations (AVMs), and/or hypervascular tumors. The compositions can be used as, for example, fillers for aneurysm sacs, AAA sac (Type II endoleaks), endoleak sealants, arterial sealants, and/or puncture sealants, and/or can be used to provide occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted. In some embodiments, a composition containing the particles can be used to prophylactically treat a condition.

The magnitude of a dose of an embolic composition can vary based on the nature, location and severity of the condition to be treated, as well as the route of administration. A physician treating the condition, disease or disorder can determine an effective amount of embolic composition. An effective amount of embolic composition refers to the amount sufficient to result in amelioration of symptoms or a prolongation of survival of the subject. The embolic compositions can be administered as pharmaceutically acceptable compositions to a subject in any therapeutically acceptable dosage, including those administered to a subject intravenously, subcutaneously, percutaneously, intratrachealy, intramuscularly, intramucosaly, intracutaneously, intra-articularly, orally or parenterally.

An embolic composition can include a mixture of particles (e.g., particles that include different types of therapeutic agents, particles that include different types of surface preferential materials), or can include particles that are all of the same type. In some embodiments, an embolic composition can be prepared with a calibrated concentration of particles for ease of delivery by a physician. A physician can select an embolic composition of a particular concentration based on, for example, the type of embolization procedure to be performed. In certain embodiments, a physician can use an embolic composition with a relatively high concentration of particles during one part of an embolization procedure, and an embolic composition with a relatively low concentration of particles during another part of the embolization procedure.

Suspensions of particles in saline solution can be prepared to remain stable (e.g., to remain suspended in solution and not settle and/or float) over a desired period of time. A suspension of particles can be stable, for example, for from about one minute to about 20 minutes (e.g. from about one minute to about ten minutes, from about two minutes to about seven minutes, from about three minutes to about six minutes).

In some embodiments, particles can be suspended in a physiological solution by matching the density of the solution to the density of the particles. In certain embodiments, the particles and/or the physiological solution can have a density of from about one gram per cubic centimeter to about 1.5 grams per cubic centimeter (e.g., from about 1.2 grams per cubic centimeter to about 1.4 grams per cubic centimeter, from about 1.2 grams per cubic centimeter to about 1.3 grams per cubic centimeter).

In some embodiments, the carrier fluid of an embolic composition can include a surfactant. The surfactant can help the particles to mix evenly in the carrier fluid and/or can decrease the likelihood of the occlusion of a delivery device (e.g., a catheter) by the particles. In some embodiments, the surfactant can enhance delivery of the embolic composition (e.g., by enhancing the wetting properties of the particles and facilitating the passage of the particles through a delivery device). In certain embodiments, the surfactant can decrease the occurrence of air entrapment by the particles in a composition (e.g., by porous particles in a composition). Examples of liquid surfactants include Tween® 80 (available from Sigma-Aldrich) and Cremophor EL® (available from Sigma-Aldrich). An example of a powder surfactant is Pluronic® F127 NF (available from BASF). In certain embodiments, an embolic composition can include from about 0.05 percent by weight to about one percent by weight (e.g., about 0.1 percent by weight, about 0.5 percent by weight) of a surfactant. A surfactant can be added to the carrier fluid prior to mixing with the particles and/or can be added to the particles prior to mixing with the carrier fluid.

Figure 3B:
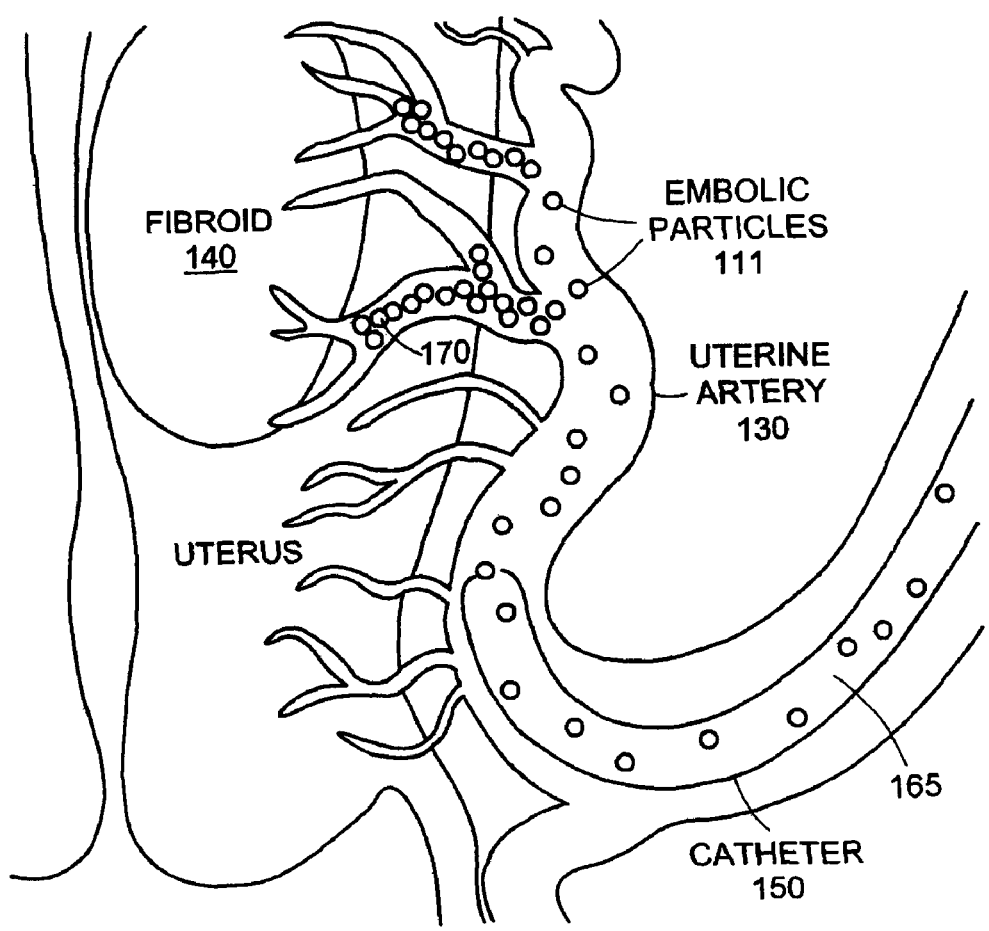
FIG. 3B is a greatly enlarged view of region 3B in FIG. 3A.

In FIGS. 3A and 3B, an embolic composition, including embolic particles 111 and a carrier fluid, is injected into a vessel through an instrument such as a catheter 150. Catheter 150 is connected to a syringe barrel 110 with a plunger 160. Catheter 150 is inserted, for example, into a femoral artery 120 of a subject. Catheter 150 delivers the embolic composition to, for example, occlude a uterine artery 130 leading to a fibroid 140. Fibroid 140 is located in the uterus of a female subject. The embolic composition is initially loaded into syringe 110. Plunger 160 of syringe 110 is then compressed to deliver the embolic composition through catheter 150 into a lumen 165 of uterine artery 130.

FIG. 3B, which is an enlarged view of section 3B of FIG. 3A, shows a uterine artery 130 that is subdivided into smaller uterine vessels 170 (e.g., having a diameter of about two millimeters or less) which feed fibroid 140. The embolic particles 111 in the embolic composition partially or totally fill the lumen of uterine artery 130, either partially or completely occluding the lumen of the uterine artery 130 that feeds uterine fibroid 140.

In some embodiments, among the particles delivered to a subject in an embolic composition, the majority (e.g., about 50 percent or more, about 60 percent or more, about 70 percent or more, about 80 percent or more, about 90 percent or more) of the particles have a diameter of about 3,000 microns or less (e.g., about 2,500 microns or less; about 2,000 microns or less; about 1,500 microns or less; about 1,200 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,200 microns or more; about 1,500 microns or more; about 2,000 microns or more; about 2,500 microns or more).

In certain embodiments, the particles delivered to a subject in an embolic composition have an arithmetic mean diameter of about 3,000 microns or less (e.g., about 2,500 microns or less; about 2,000 microns or less; about 1,500 microns or less; about 1,200 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,200 microns or more; about 1,500 microns or more; about 2,000 microns or more; about 2,500 microns or more). Exemplary ranges for the arithmetic mean diameter of particles delivered to a subject include from about 100 microns to about 500 microns; from about 100 microns to about 300 microns; from about 300 microns to about 500 microns; from about 500 microns to about 700 microns; and from about 900 microns to about 1,200 microns. In general, the particles delivered to a subject in an embolic composition have an arithmetic mean diameter in approximately the middle of the range of the diameters of the individual particles, and a variance of about 20 percent or less (e.g. about 15 percent or less, about ten percent or less).

In some embodiments, the arithmetic mean diameter of the particles delivered to a subject in an embolic composition can vary depending upon the particular condition to be treated. As an example, in embodiments in which the particles in an embolic composition are used to treat a liver tumor, the particles delivered to the subject can have an arithmetic mean diameter of about 500 microns or less (e.g., from about 100 microns to about 300 microns; from about 300 microns to about 500 microns). As another example, in embodiments in which the particles in an embolic composition are used to treat a uterine fibroid, the particles delivered to the subject in an embolic composition can have an arithmetic mean diameter of about 1,200 microns or less (e.g., from about 500 microns to about 700 microns; from about 700 microns to about 900 microns; from about 900 microns to about 1,200 microns).

The arithmetic mean diameter of a group of particles can be determined using a Beckman Coulter RapidVUE Image Analyzer version 2.06 (Beckman Coulter, Miami, Fla.), described above. The arithmetic mean diameter of a group of particles (e.g., in a composition) can be determined by dividing the sum of the diameters of all of the particles in the group by the number of particles in the group.

While certain embodiments have been described, the invention is not so limited.

As an example, in some embodiments a particle can be coated (e.g., with a bioabsorbable material). For example, a particle can include a polyvinyl alcohol matrix material, a surface preferential material that includes segmented polyurethane/DABs, polyethylene tetramethylene oxide, and a fraction of BA-L™, and a sodium alginate coating. The coating can contain, for example, one or more therapeutic agents, or can be substantially free of therapeutic agents. In certain embodiments, a particle can be coated to include a high concentration of one or more therapeutic agents that can alternatively or additionally be loaded into surface preferential material 14 and/or matrix material 12 of particle 10. The coating can release an initial dosage of therapeutic agent after which the body of the particle (e.g., region I and region S) can provide a burst release of therapeutic agent. The therapeutic agent in the coating can be the same as or different from the therapeutic agent in the body, region S, and/or region I of the particle. The therapeutic agent in the coating can be applied, for example, by exposing the particle to a high concentration solution of the therapeutic agent. Coatings are described, for example, in U.S. patent application Ser. No. 10/615,276, filed on Jul. 8, 2003, and entitled "Agent Delivery Particle", which is incorporated herein by reference.

In some embodiments, the coating can be, for example, a degradable and/or bioabsorbable polymer which erodes when the particle is administered. The coating can assist in controlling the rate at which therapeutic agent is released from the particle (e.g., from the surface preferential material). For example, the coating can be in the form of a porous membrane. The coating can delay an initial burst of therapeutic agent release. The coating can be applied by dipping or spraying the particle. The erodible polymer can be a polysaccharide (such as an alginate) or a polysaccharide derivative. In some embodiments, the coating can be an inorganic, ionic salt. Other erodible coatings include water soluble polymers (such as polyvinyl alcohol, e.g., that has not been cross-linked), biodegradable poly DL-lactide-poly ethylene glycol (PELA), hydrogels (e.g., polyacrylic acid, haluronic acid, gelatin, carboxymethyl cellulose), polyethylene glycols (PEG), chitosan, polyesters (e.g., polycaprolactones), and poly(lactic-co-glycolic) acids (e.g., poly(d-lactic-co-glycolic) acids). A polymer coating, e.g. an erodible coating, can be applied to the particle surface in embodiments in which a high concentration of therapeutic agent has not been applied to the particle surface.

As an additional example, in some embodiments one or more particles is/are substantially nonspherical. In some embodiments, particles can be shaped (e.g., molded, compressed, punched, and/or agglomerated with other particles) at different points in the particle manufacturing process. In some embodiments (e.g., where matrix material 12 is a polymer such as a polyvinyl alcohol, and the gelling precursor is sodium alginate), after contacting the particles with the gelling agent but before cross-linking, the particles can be physically deformed into a specific shape and/or size. After shaping, the polymer matrix material 12 (e.g., polyvinyl alcohol) can be cross-linked, optionally followed by substantial removal of the gelling precursor (e.g., alginate). While substantially spherical particles are preferred, non-spherical particles can be manufactured and formed by controlling, for example, drop formation conditions. In some embodiments, nonspherical particles can be formed by post-processing the particles (e.g., by cutting or dicing into other shapes). Particle shaping is described, for example, in Baldwin et al., copending U.S. Published Patent Application No. US 2003/0203985 A1, which is incorporated herein by reference.

As a further example, in some embodiments the particles can be used for tissue bulking As an example, the particles can be placed (e.g., injected) into tissue adjacent to a body passageway. The particles can narrow the passageway, thereby providing bulk and allowing the tissue to constrict the passageway more easily. The particles can be placed in the tissue according to a number of different methods, for example, percutaneously, laparoscopically, and/or through a catheter. In certain embodiments, a cavity can be formed in the tissue, and the particles can be placed in the cavity. Particle tissue bulking can be used to treat, for example, intrinsic sphincteric deficiency (ISD), vesicoureteral reflux, gastroesophageal reflux disease (GERD), and/or vocal cord paralysis (e.g., to restore glottic competence in cases of paralytic dysphonia). In some embodiments, particle tissue bulking can be used to treat urinary incontinence and/or fecal incontinence. The particles can be used as a graft material or a filler to fill and/or to smooth out soft tissue defects, such as for reconstructive or cosmetic applications (e.g., surgery). Examples of soft tissue defect applications include cleft lips, scars (e.g., depressed scars from chicken pox or acne scars), indentations resulting from liposuction, wrinkles (e.g., glabella frown wrinkles), and soft tissue augmentation of thin lips. Tissue bulking is described, for example, in Bourne et al., copending U.S. Published Patent Application No. US 2003/0233150 A1, which is incorporated herein by reference.

As another example, the particles can include other materials. For example, the particles can include (e.g., encapsulate) diagnostic agent(s) such as a radiopaque material, an MRI-visible material, a ferromagnetic material, and/or an ultrasound contrast agent. In some embodiments, surface preferential material 14 can include one or more of these diagnostic agents. Diagnostic agents are described, for example, in U.S. patent application Ser. No. 10/651,475, filed on Aug. 29, 2003, and entitled "Embolization", which is incorporated herein by reference.

As another example, in some embodiments particle 10 does not include a therapeutic agent (e.g., a therapeutic agent is not bound to surface preferential material 14).

As a further example, in some embodiments a particle can be formed without pores (nonporous particle).

As another example, in some embodiments a particle can include multiple (e.g., two, three, four, five, six) different surface preferential materials.

As an additional example, in some embodiments, it can be desirable to reduce the surface tension of the mixture contained in gelling vessel 320 (e.g., when forming particles having a diameter of about 500 microns or less). This can be achieved, for example, by heating the mixture in gelling vessel 320 (e.g., to a temperature greater than room temperature, such as a temperature of about 30° C. or more), by bubbling a gas (e.g., air, nitrogen, argon, krypton, helium, neon) through the mixture contained in gelling vessel 320, by stirring (e.g., via a magnetic stirrer) the mixture contained in gelling vessel 320, by including a surfactant in the mixture containing the gelling agent, and/or by forming a mist containing the gelling agent above the mixture contained in gelling vessel 320 (e.g., to reduce the formation of tails and/or enhance the sphericity of the particles).

Other embodiments are in the claims.

What is claimed is:

1. A particle comprising a first polymer, the particle having an interior region and a surface region, a weight percent of the first polymer in the interior region of the particle being less than a weight percent of the first polymer at the surface region of the particle, and the particle having a diameter of from about ten microns to about 3,000 microns,
wherein the first polymer has the formula D-B-[O-(A-O)$_n$-B]$_m$-D, where O is a first oligomeric segment, B is a first coupling segment, A is a second coupling segment, D is a polyfluoro oligomeric group, m is from one to 20, and n is from zero to 20.

2. The particle of claim 1, wherein the interior region is devoid of the first polymer.

3. The particle of claim 1, wherein the interior region comprises at most 50 weight percent of the first polymer.

4. The particle of claim 3, wherein the particle comprises from about 0.1 weight percent to about 90 weight percent of the first polymer.

5. The particle of claim 1, wherein the interior region comprises at least 0.1 weight percent of the first polymer.

6. The particle of claim 1, wherein the surface region comprises at least 0.1 weight percent of the first polymer.

7. The particle of claim 6, wherein the particle comprises from about 0.1 weight percent to about 90 weight percent of the first polymer.

8. The particle of claim 1, wherein the surface region comprises at most 100 weight percent of the first polymer.

9. The particle of claim 1, wherein the difference between the weight percent of the first polymer in the interior region and the weight percent of the first polymer at the surface region is at least 30 weight percent.

10. The particle of claim 1, wherein the particle has a diameter of at least 100 microns.

11. The particle of claim 1, wherein the particle has a diameter of at most 2,500 microns.

12. The particle of claim 1, wherein the first polymer comprises a backbone and side groups that are more polar than the backbone.

13. The particle of claim 1, wherein the first polymer has a molecular weight of from about 500 to about 15,000.

14. The particle of claim 1, wherein the first polymer is linear.

15. The particle of claim 1, wherein O comprises a member selected from the group consisting of polyurethanes, polyureas, polyamides, polyalkylene oxides, polycarbonates, polyesters, polylactones, polysilicones, polyethersulfones, polyolefins, polyvinyls, polypeptide polysaccharides, and ether and amine linked segments thereof.

16. The particle of claim 1, wherein A comprises a member selected from the group consisting of diamines, diisocyanates, disulfonic acids, dicarboxylic acids, diacid chlorides, and dialdehydes.

17. The particle of claim 1, wherein B comprises a member selected from the group consisting of diamines, diisocyanates, disulfonic acids, dicarboxylic acids, diacid chlorides, and dialdehydes.

18. The particle of claim 17, wherein B further comprises a functional group selected from the group consisting of esters, carboxylic acid salts, sulfonic acid salts, phosphonic acid salts, thiols, vinyls, and secondary amines.

19. The particle of claim 1, wherein D comprises $CF_3(CF_2)_pCH_2CH_2-$, wherein p is from two to 20.

20. The particle of claim 1, wherein D comprises $CF_3(CF_2)_m(CH_2CH_2O)_q$-, wherein m is from one to 20 and q is from one to ten.

21. The particle of claim 1, wherein the particle further comprises a therapeutic agent.

22. The particle of claim 1, wherein the particle further comprises a therapeutic agent.

23. The particle of claim 1, wherein the particle further comprises a second polymer.

24. The particle of claim 23, wherein the second polymer comprises a member selected from the group consisting of polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co-glycolic) acids, and combinations thereof.

25. The particle of claim 23, wherein the particle further comprises a therapeutic agent.

26. The particle of claim 25, wherein the therapeutic agent is bound to the first polymer.

27. The particle of claim 1, wherein the particle further comprises a polysaccharide.

28. The particle of claim 1, wherein the particle is spherical.

29. The particle of claim 1, wherein the particle further comprises a coating disposed over the surface region.

30. The particle of claim 29, wherein the coating is bioabsorbable.

31. The particle of claim 1, wherein the particle comprises from about 0.25 weight percent to about 50 weight percent of the first polymer.

32. The particle of claim 1, wherein the particle comprises from about 15 weight percent to about 35 weight percent of the first polymer.

33. The particle of claim 1, wherein the interior region has a density of large pores and the surface region has a density of large pores, and the density of large pores of the interior region is greater than the density of large pores at the surface region.

* * * * *